US007078423B2

(12) United States Patent
Nivorozhkin et al.

(10) Patent No.: US 7,078,423 B2
(45) Date of Patent: Jul. 18, 2006

(54) 5-ARYLTETRAZOLE COMPOUNDS, COMPOSITIONS THEREOF, AND USES THEREFOR

(75) Inventors: Alex Nivorozhkin, West Roxbury, MA (US); John Van Duzer, Georgetown, MA (US); Andrew Salzman, Belmont, MA (US); Garry Southan, Lynn, MA (US); Siya Ram, Winchester, MA (US); Qi Zeng, North Andover, MA (US); Csaba Szabo, Gloucester, MA (US)

(73) Assignee: Inotek Pharmaceuticals Corporation, Beverly, MA (US)

( * ) Notice: Subject to any disclaimer, the term of this patent is extended or adjusted under 35 U.S.C. 154(b) by 0 days.

(21) Appl. No.: 10/197,609

(22) Filed: Jul. 18, 2002

(65) Prior Publication Data

US 2004/0019208 A1    Jan. 29, 2004

(51) Int. Cl.
*A61K 31/41* (2006.01)
*C07D 257/04* (2006.01)

(52) U.S. Cl. ..................................... 514/381; 548/253
(58) Field of Classification Search ................ 548/253; 514/381
See application file for complete search history.

(56) References Cited

U.S. PATENT DOCUMENTS

| 5,049,572 | A | * | 9/1991 | Scherrer et al. |
| 5,232,937 | A | | 8/1993 | Makovec et al. |
| 5,284,954 | A | | 2/1994 | Wittenberger |
| 5,364,869 | A | | 11/1994 | De |
| 5,663,357 | A | | 9/1997 | Teng et al. |
| 5,874,593 | A | | 2/1999 | Ushio |
| 5,976,576 | A | | 11/1999 | Makovec et al. |
| 6,191,136 | B1 | | 2/2001 | Marban |
| 6,191,289 | B1 | | 2/2001 | Ushio |
| 6,277,998 | B1 | | 8/2001 | Ushio |
| 6,281,222 | B1 | | 8/2001 | Salzman et al. |
| 6,297,261 | B1 | | 10/2001 | Christophersen et al. |
| 6,388,088 | B1 | | 5/2002 | Sidduri |
| 6,417,393 | B1 | | 7/2002 | Christophersen et al. |
| 6,569,862 | B1 | | 5/2003 | Marban |
| 2002/0032210 | A1 | | 3/2002 | Dahl et al. |
| 2002/0037905 | A1 | | 3/2002 | Dahl et al. |
| 2002/0103202 | A1 | | 8/2002 | Pinto et al. |
| 2003/0186998 | A1 | | 10/2003 | Marban |
| 2003/0229120 | A1 | | 12/2003 | Olsen et al. |

FOREIGN PATENT DOCUMENTS

| EP | 0 638 553 | 7/1994 |
| JP | 10025294 | 1/1998 |
| WO | 90/09989 | 9/1990 |
| WO | 93/16053 | 8/1993 |
| WO | 98/58522 | 12/1998 |
| WO | 99/24442 | 5/1999 |
| WO | WO 99/24038 | 5/1999 |
| WO | 00/16798 | 3/2000 |
| WO | 00/24707 | 5/2000 |
| WO | 00/28979 | 5/2000 |
| WO | 00/64888 | 11/2000 |
| WO | 01/66098 | 9/2001 |
| WO | WO 01/85705 | 11/2001 |
| WO | 02/00647 | 1/2002 |
| WO | WO 02/00647 | 1/2002 |

OTHER PUBLICATIONS

Oda, T., Akaike, T., Hamamoto, T., Suzuki, F., Hirano, T., and Maeda, H. 1989. Oxygen radicals in influenza-induced pathogenesis and treatment with pyran polymer-conjugated SOD. *Science* 244-974-976.

Tan, S., Yokoyama, Y., Dickens, E., Cash, T.G., Freeman, B.A., and Parks, D.A. 1993. Xanthine oxidase activity in the circulation of rats following hemorrhagic shock. *Free Radic. Biot Med* 15:407-4 14.

McCord, J.M. 1985. Oxygen-derived free radicals in postischemic tissue injury. *New Engl .J. Med.* 3 12:159-163.

Miesel, R., Zuber, M., Sanocka, D., Graetz, R., and Kroeger, H. 1994. Effects of allopurinol on in vivo suppression of arthritis in mice and ex vivo modulation of phagocytic production of oxygen radicals in whole human blood. *Inflammation.* 18:597-612.

Engerson, T.D., MeKelvey, T.G., Rhyne, D.B., Boggio, E.B., Snyder, S.J., and Jones, H.P. 1987. The conversion of xanthine dehydrogenase to oxidase in ischaemic rat tissue. *J. Clin. Invest.* 79:1564-1570.

Akaike, T., Ando, M., Tatsuya, 0., Doi, T., Ijiri, S., Araki, S., and Maeda, H. 1990. Dependence on 02 generation by xanthine oxidase of pathogenesis of influenza virus infection in mice. *J. Clin. Invest.* 85:739-745.

Mohacsi, A.; Kozlovsky, B.; Kiss, I.; Seres, I.; Fulop, T.; Neutrophils obtained from obliterative atherosclerotic patients exhibit enchanced resting respiratory burrst and increased degranulation in response to various stimuli. *Biochimica et Biophysica Acta,* 1316 (1996) 210-216.

Friedi, H.P., Smith, D.J., Till G.0., Thomson, P.D., Louis, D.S., and Ward, P.A. 1990. Ischemia-reperfusion in humans. Appearance of xanthine oxidase activity. *Am J Path* 136:491-495.

Friedl, H.P., Till, G.0., Trentz, 0., and Ward, P.A. 1989. Role of histamine, complement and xanthine oxidase in thermal injury of the skin. *Am J Path* 135:203-2 17.

(Continued)

Primary Examiner—Taofiq Solola
(74) Attorney, Agent, or Firm—Wilmer Cutler Pickering Hale and Dorr LLP

(57) ABSTRACT

The present invention relates to 5-Aryltetrazole compounds, compositions comprising a 5-Aryltetrazole compound, and methods for treating an inflammation disease, a reperfusion disease, hyperuricemia, gout, or tumor-lysis syndrome in an animal in need thereof comprising administering to the animal an effective amount of a 5-Aryltetrazole compound.

50 Claims, No Drawings

OTHER PUBLICATIONS

Parks, D.A., Bulkley, G.B., and Granger, D.N. 1983. Role of oxygen free radicals in shock, ischemia, and organ preservation. *Surgery* 94:428-432.

Demling, R., LaLonde, C., Youn, Y.K., Daryani, R., Campbell, C., and Knox, J. 1992. Lung oxidant changes after zymosan peritonitis: relationship between physiologic and biochemical changes. *Am Rev Respir Dis* 146:1272-1278.

Chambers, D.E., Parks, D.A., Patterson, G., Roy, R., McCord, J.M., Yoshida, S., Parmley, L.F., and Downey, J.M. 1985. Xanthine oxidase as a source of free radical damage in myocardial ischemia. *J Mol Cell Cardiol* 17:145-152.

Deitch, E.A., Bridges, W., Baker, J., Ma, J.W., Ma, L., Grisham, M.B., Granger, D.N., Specian, R.D., and Berg, R. 1988. Hemorrhagic shock-induced bacterial translocation is reduced by xanthine oxidase inhibition or inactivation. *Surgery* 104:191-198.

Mayumi, T., Chan, C.K., Clemens, M.G., and Bulkley, G.B. 1996. Zonal heterogeneity of hepatic injury following shock/resusciation: relationship of xanthine oxidase activity to localization of neutrophil accumulation and central lobular necrosis. *Shock* 5:324-332.

Flynn, W.J.Jr. and Hoover, E.L. 1994. Allopurinol plus standard resuscitation preserves hepatic blood flow and function following hemorrhagic shock. *J Trauma* 37:956-961.

Flynn, W.J.Jr., Pilati, D., and Hoover, E.L. 1997. Xanthine oxidase inhibition prevents mesenteric blood flow deficits after resuscitated hemorrhagic shock by preserving endothelial function. *J Surg Res* 68:175-180.

Mannion, D., Fitzpatrick, G.J., and Feeley, M. 1994. Role of xanthine oxidase inhibition in survival from hemorrhagic shock. *Circ Shock* 42:39-43.

Cunningham, S.K. and Keaveny, T.V. 1978. Effect of a xanthine oxidase inhibitor on adenine nucleotide degradation in hemorrhagic shock. *Eur Surg. Res.* 10:305-313.

Youn, Y.K., LaLonde, C., and Demling, R. 1992. Oxidants and the pathophysiology of burn and smoke inhalation injury. *Free Radic. Biol. Med.* 12:409-415.

Deitch, E.A., Kemper, A.C., Specian, R.D., and Berg, R.D. 1992. A study the relationship among survival, gut-origin sepsis, and bacterial translocation in a model of systemic inflammation. *J Trauma* 32:141-147.

Anderson, B.O., Moore, E.E., Moore, F.A., Left J. A., Terada, L.S., Harken, A.H., and Repine, J.E. 1991. Hypovolemic shock promotes neutrophil sequestration in lungs by a xanthine oxidase-related mechanism. *J Appl Physiol* 71:1862-1865.

Poggetti, R.S., Moore, F.A., Moore, E.E., Koeike, K., and Banerjee, A. 1992. Simultaneous liver and lung injury following gut ischemia is mediated by xanthine oxidase. *J Trauma* 32:723-727.

Nielsen, V.G., McCammon, A.T., Tan, S., Kirk, K.A., Samuelson, P.N., and Parks, D.A. 1995. Xanthine oxidase inactivation attenuates postocclusion shock after descending thoracic aorta occlusion and reperfusion in rabbits. *J Thorac. Cardiovasc Surg.* 110:715-722.

Schwartz, M.D., Repine, J. E., and Abraham, E. 1995. Xanthine oxidase-derived oxygen radicals increase lung cytokine epression in mice subjected to hemorrhagic shock. *Am J Respir Cell Mol Biol* 12:434-440.

Crowell, J.W., Jones, C.E., and Smith, E.E. 1969. Effect of allopurinol on hemorrhagic shock. *Am J Phys* 216:744-748.

Linder, N., Rapola, J., and Raivio, K.O. 1999. Cellular expression of xanthine oxidoreductase protein in normal human tissues. *Lab Invest* 79:967-974.

Saksela, M., Lapatto, R., and Raivio, K.O. 1998. Xanthine oxidoreductase gene expression and enzyme activity in developing human tissues. *Biol Neonate* 74:274-280.

Battelli, M.G., Abbondanza, A., Musiani, S., Buonamici, L., Strocchi, P., Tazzari, P.L., Gramantieri, L., and Stirpe, F. 1999. Determination of xanthine oxidase in human serum by a competitive enzyme-linked immunosorbent assay (ELISA). *Clin Chim Acta* 281:147-158.

Houston, M., Estevez, A., Chumley, P., Aslan, M., Marklund, S., Parks, D.A., and Freeman, B.A. 1999. Binding of xanthine oxidase to vascular endothelium. Kinetic characterization and oxidative impairment of nitric oxide-dependent signaling. *J Biol Chem* 274:4985-4994.

Fox, N.E. and van Kuijk, F.J. 1998. Immunohistochemical localization of xanthine oxidase in human retina. *Free Radic Biol Med* 24:900-905.

Rouquette, M., p., 5., Bryant, R., Benboubetra, M., Stevens, C.R., Blake, D.R., Whish, W.D., Harrison, R., and Tosh, D. 1998. Xanthine oxidoreductase is asymmetirically localized on the outer surface of human endothelial and epithelial cells in culture. *FEBS Lett* 426:397-401.

Cardillo, C., Kilcoyne, C.M., Cannon, R.O.3., Quyyumi, A.A., and Pauza, J.A. 1997. Xanthine oxidase inhibition with oxypurinol improves vasodilator function in hypercholesterlemic but not in hypertensive patients. *Hypertension* 30:57-63.

Page, S., Powell, D., Benboubetra, M., Stevens, C.R., Blake, D.R., Selase, F., Wolstenholme, A.J., and Harrison, R. 1998. Xanthine oxidoreductase in human mammary epithelial cells: activation in response to inflammatory cytokines. *Biochim Biophys Acta* 1381:191-202.

Zhang, Z., Naughton, D., Winyard, P.G., Benjamin, N., Blake, D.R., and Symons, M.C. 1998. Generation of nitric oxide by a nitrite reductase activity of xanthine oxidase: a potential pathway for nitric oxide formation in the absence of nitric oxide synthase activity. *Biochem Biophys Res Commun* 249:767-772.

Trujillo, M., Alvarez, M.N., Peluffo, G., Freeman, B.A., and Radi, R. 1998. Xanthine oxidase-mediated decomposition of 5-nitrosothiols. *J. Biot Chem.* 273:7828-7834.

S. E. Goldfinger, New Eng. £ Med. 285, 1303 (1971).

R. L. Buchanan, V. Spranomanis and R.A. Partyka, Hypocholesterolemic 5-substituted tetrazoles. *J. Med. Chem.* 12,1001(1969).

J.S. Shukla and R. Rastogi, Studies on neuorpharmacological and biochemical properties of 5-substituted tetrazoles. *Indian J Physiol Pharmacol.* 25, 369 (1981).

R. H. Springer, M .K. Dimmitt, T. Novinson, D. E. O Brien, R. K. Robins, L. N Simon and J.P. Miller, *J. Med. Chem.,* 19, 291 (1916): U.S. Patent 4, 021, 556.

H.E.Skipper, R.K. Robins and R.J. Thompson,. Inhibition of experimental neoplasms by 4-aminopyrazolo[3,4-d]pyrimidine. *Proc. Soc. Exp. Blot Med.* 89, 594 (1955).

Z. P. Demko, K. B. Sharpless, *J. Org. Chem.,* 66, 2458 (2001).

R. N. Butler, In *Comprehensive Heterocyclic Chemistry;* Katritzky, A. R., Rees, C. W., Scriven, E. F. V., Eds.; Pergamon: Oxford, U. K., 1996, vol. 4.

Tyuzo Isida, et al. The Formation of Tin-Nitrogen Bonds. V. The selective 1-Substitution Reaction of 5-Substituted 2-(Tri-n-butylstannyl tetrazoles with Methyl Iodide, Methyl p-Toluenesulfonate, Dimethyl Sulfate, and Ethyl Bromoacetate. *Chemical Society of Japan*, vol. 46, 2176-2180 (1973).

Rosenbaum, et al. Thermolyse von 1-Thiocarbamoyl-5-phenyl-tetrazolen: J. Prakt. Chem. 334 (1992) 283-284.

A. Konnecke et al. Tetrahedron Letters No. 7, pp 533-536, 1976. Pergamon Press.

Branko S. Jursic. N. Acyltetrazole As An Intermediate for Preparation of Carboxylic Acid Derivatives. Synthetic Communications, 23(3), 361-364(1993).

J.J Baldwin et al. 4-Trifluoromethylimidazoles and 5-(4-Pyridyl)-1,2,4-triazoles, New Classes of Xanthine Oxidase Inhibitors: *Journal of Medicinal Chemistry*, 1975, vol. 18, No. 9.

Journal of Organic Chemistry of the USSR, Russian Original vol. 20, No. 5, Part 2, May, 1984.

S.J. Czuczwar et al. (1998) "A potential anti-asthmatic drug, CR 2039, enhances the anticonvulsive activity of some antiepileptic drugs against pentetrazol in mice" *European Neuropsychopharmacology*, 8(3), pp. 233-238 (1998).

S.J. Czuzwar et al. (1996) "Influence of a potential anti-asthmatic drug, CR 2039, upon the anticonvulsive activity of conventional antiepileptics against maximal electroshock-induced seizures in mice" *J Neural Transm.* 103(12), pp. 1371-1378 (1996).

Francesco Makovec (1992) "Antiallergic and Cytoprotective Activity of New N-Phenylbenzamide Acid Derivatives" *J. Med Chem.* 35(20), pp. 3633-3640 (1992).

Laura Revel et al. (1992) "CR 2039, a new bis-(1H-tetrazol-5-yl) phenylbenzamide derivative with potential for the topical treatment of asthma" *Eur. J. Pharmacology*, 229 (1), pp. 45-53 (1992).

L. Revel et al.(1992) "Pharmacological profile of CR 2039 (Dizolast) a new agent for the treatment of allergic diseases" *Life Sciences,* 229, pp. 273-277 (1992).

S. Persiani et al. (2001) Pharmacokinetics of andolast after administration of single escalating doses by inhalation in mild asthmatic patients, *Biopharmaceutics & Drug Disposition,* 22: 73-81, (2001).

International Search Report, PCT/US03/22462, mailed Dec. 11, 2003.

Blake et al., 1997, "Xanthine Oxidase: Four Roles for the Enzyme in Rheumatoid Pathology" Biochemical Society Transactions, 25:1-7.

Boros et al., 1989, "Oxygen Free Radical-Induced Histamine Release During Intestinal Ischemia and Reperfusion", Eur. Surg. Res. 21:297-304.

Brown et al., 1988, "Xanthine Oxidase Produces Hydrogen Peroxide which Contributes to Reperfusion Injury of Ischemic, Isolated, Perfused Rat Hearts", J. Clin. Invest. 81:1297-301.

Deliconstantinos et al., 1996, "Alterations of Nitric Oxide Synthase and Xanthine Oxidase Activities of Human Keratinocytes by Ultraviolet B Radiation", Biochem. Pharm. 51:1727-1738.

Harrison, R., 1997, "Human Xanthine oxidoreductase: In Search of a Function", Biochemical Society Transactions 25: 1-7.

Ketai et al., Plasma hypoxanthine and exercise. *Am Rev Respir Dis.* Jul. 1987;136(1):98-101.

Zollei et al., Experimental study of hypovolaemic shock-induced gastric mucosal lesions in the rat. *Ann Acad Med Singapore.* Jan. 1999;28(1):85-9.

Flynn et al., Xanthine oxidase inhibition after resuscitated hemorrhagic shock restores mesenteric blood flow without vasodilation. *Shock.* Oct. 1997;8(4):300-4.

Modelska et al., Inhibition of beta-adrenergic-dependent alveolar epithelial clearance by oxidant mechanisms after hemorrhagic shock. *Am J Physiol.* May 1999;276(5 Pt 1):L844-57.

Myznikov et al., Tetrazoles XXV. Production of N-benzoyltetrazoles and their chemical characteristics. *J. Org. Chem. USSR* Dec. 20, 1988, 24(7):1397-1401.

Oshipova et al., Tetrazoles XIX. Acylation of tetrazoles under the conditions of phase-transfer catlysis. *J. Org. Chem. USSR* 1984 20(11):2248-2252.

Ichibuchi et al., Synthesis and structure-activity relationships of 1-phenylpyrazoles as xanthine oxidase inhibitors. *Bioorg. Med. Chem. Lett.* 2001 11(7):879-882.

Nagamatsu et al., Novel xanthine oxidase inhibitor studies. Part 2. Synthesis and xanthine oxidase inhibitory activities of 2-substituted 6-alkyl-indenehydrazino- or 6-arylmethylijndenenehydrazino-7H-purines and 3- and/or 5-substituted 9H-1,2,4-triazoleo[3,4-i]purines, *J. Chem. Soc. Perkin Trans. 1* 1999 3117-3125.

Vorbach et al., The housekeeping gene xanthine oxidoreductase is necessary for milk fat droplet enveloping and secretion: gene sharing in the lactating mammary gland. *Genes Dev.* Dec. 15, 2002;16(24):3223-35.

Ketai et al., Plasma hypoxanthine and exercise. *Am Rev Respir Dis* 136(1):98-101 (1987).

Zollei et al., Experimental study of hypovolaemic shock-induced gastric mucosal lesions in the rat. *Ann Acad Med Singapore.* 28(1):85-9 (1999).

Flynn et al., Xanthine oxidase inhibition after resuscitated hemorrhagic shock restores mesenteric blood flow without vasodilation. *Shock* 8(4):300-4 (1997).

Modelska et al., Inhibition of beta-adrenergic-dependent alveolar epithelial clearance by oxidant mechanisms after hemorrhagic shock. *Am J Physiol.* 276(5 Pt 1):L844-57 (1999).

Myznikkov et al., Tetrazoles XXV. Production of N-benzoyltetrazoles and their chemical characteristics. *J. Org. Chem. USSR* 24(7):1397-1401 (1988).

Oshipova et al., Tetrazoles XIX. Acylation of tetrazoles under the conditions of phase-transfer catlysis. *J. Org. Chem. USSR* 20(11):2248-2252 (1984).

Ichibuchi et al., Synthesis and structure-activity relationships of 1-phenylpyrazoles as xanthine oxidase inhibitors. *Bioorg. Med. Chem. Lett.* 11(7):879-882 (2001).

Nagamatsu et al., Novel xanthine oxidase inhibitor studies. Part 2. Synthesis and xanthine oxidase inhibitory activities of 2-substituted 6-alkylindenehydrazino- or 6-arylmethylijndenenehydrazino-7H-purines and 3- and/or 5-substituted 9H-1,2,4-triazoleo[3,4-i]purines. *J. Chem. Soc. Perkin Trans. 1* 3117-3125 (1999).

Vorbach et al., The housekeeping gene xanthine oxidoreductuctase is necessary for milk fat droplet enveloping and secretion: gene sharing in the lactating mammary gland. *Genes and Dev* 16(24):3223-3235 (2002).

* cited by examiner

5-ARYLTETRAZOLE COMPOUNDS, COMPOSITIONS THEREOF, AND USES THEREFOR

GOVERNMENTAL SUPPORT

The research leading to the invention was supported, at least in part, by a grant from the National Institute of General Medical Sciences Grant No. 1R43 GM63274-01A1; the National Heart, Lung, and Blood Institute Grant No. 1R43HL70342-01; the National Institute of General Medical Sciences Grant No. 2R44GM59017-02; and the National Institute of General Medical Sciences Grant No. 1R43GM59017-01. Accordingly, the U.S. Government may have certain rights in the invention.

1. FIELD OF THE INVENTION

The present invention relates to 5-Aryltetrazole Compounds, compositions comprising a 5-Aryltetrazole Compound, and methods for treating or preventing an inflammation disease, a reperfusion disease, hyperuricemia, gout, or tumor-lysis syndrome in an animal in need thereof comprising administering to the animal an effective amount of a 5-Aryltetrazole Compound.

2. BACKGROUND OF THE INVENTION

The level of xanthine oxidase ("XO") in an animal increases markedly (>400-fold in bronchoalveolar fluid in pneumonitis) during inflammation, ischemia-reperfusion injury, and atherosclerosis. Particularly, due to the spillover of tissue XO into the circulation, plasma levels of XO may be detected in an animal experiencing adult respiratory distress syndrome, ischemia-reperfusion injury, arthritis, sepsis, hemorrhagic shock, and other inflammatory conditions. Inflammatory-induced histamine release by mast cells and basophils also enhances the activity of XO.

Superoxide radical ($O_2^-$) can be generated by xanthine oxidase and NADPH oxidase from the partial reduction of molecular oxygen. Neutrophils and macrophages are known to produce $O_2^-$ and hydrogen peroxide ($H_2O_2$), which normally are involved in the killing of ingested or invading microbes (T. Oda et al., Science, 244:974–976). Under physiologic conditions XO is ubiquitously present in the form of a xanthine dehydrogenase (XDH). XDH is a molybdenum iron-sulfur flavin dehydrogenase that uses $NAD^+$ as an electron acceptor to oxidize purines, pyrimidines, pteridins, and other heterocyclic nitrogen-containing compounds. In mammals, XDH is converted from the NAD-dependent dehydrogenase form to the oxygen-dependent oxidase form, either by reversible sulfhydryl oxidation or irreversible proteolytic modification (S. Tan et al., Free Radic. Biol. Med. 15:407–414). Xanthine oxidase then no longer uses $NAD^+$ as an electron acceptor, but transfers electrons onto oxygen, generating $O^{2-}$, $H_2O_2$, and hydroxyl radical (OH) as purines are degraded to uric acid (J. M. McCord et al., New Engl. J. Med. 312:159–163; R. Miesel et al., Inflammation, 18:597–612). Inflammatory activation converts XDH to XO, mainly by oxidizing structurally important thiolates. Inflammation also markedly up-regulates the conversion of xanthine dehydrogenase (T. D. Engerson et al., J. Clin. Invest. 79:1564–1570).

Inhibition of XO activity blocks the formation of $O_2^-$ and prevents loss of purine nucleotides, and is therefore salutary in a variety of shock and ischemia reperfusion disorders. Pharmacologic inhibition of XO can also be beneficial by blocking the pro-inflammatory effect of $O_2^-$ on gene expression (M. D. Schwartz et al., Am. J. Respir. Cell. Mol. Biol., 12:434–440). $O_2^-$ has been implicated in the nuclear translocation of NF-kappa B and the expression of NF-icB-dependent genes. In mice subjected to hemorrhagic shock, depletion of XO by a tungsten-enriched diet decreased mononuclear mRNA levels of IL-113 and TNF-a. Similar results were obtained after pharmacologic inhibition of XO by in vivo administration of allopurinol. A vicious cycle can be created by oxidant stress, in which $O_2^-$ induction of pro-inflammatory cytokines results in greater XDH to XO conversion, and thus more $O_2^-$ production. This suggests that XO inhibitors can exert important anti-inflammatory actions by interrupting this process at multiple points, in particular, by blocking pro-inflammatory gene expression.

Pharmacologic inhibition of XO can also be beneficial in hemorrhagic shock by preserving the intracellular nucleotide pool. Under conditions of energetic failure, induced by hypoxia or by oxidant-induced poly(ADP-ribose) synthetase activation, high-energy phosphate nucleotides are sequentially degraded to inosine monophosphate→xanthine→hypoxanthine. In the presence of XO and molecular oxygen, xanthine and hypoxanthine degrade to uric acid, thereby depleting the purine pool. The loss of available purines with which to form ATP accelerates the loss of intracellular energetics and contributes to cell necrosis and organ failure. XO inhibitors block this terminal degradative pathway and permit the cell to recover and reestablish adequate stores of high energy phosphate nucleotides. In a canine model of severe hemorrhagic shock, pre-treatment with allopurinol resulted in a 6-fold increase in survival (J. W. Crowell et al., Am. J. Phys. 216:744–748). When the administration of allopurinol was delayed until after shock had been produced, allopurinol exerted no benefit. Infusion of the purine base hypoxanthine after the onset of shock similarly provided no benefit. When allopurinol and hypoxanthine were co-infused, however, there was a dramatic increase in survival (no survival in control group at 16 hours post-shock vs. a 40% survival in the treated group at 48 hours). Similar results were obtained in a canine model of hemorrhagic shock in which allopurinol significantly improved survival, whereas a cocktail of free-radical scavengers (superoxide dismutase, catalase, dimethylsulfoxide, and alpha tocopherol) had no effect (D. Mannion, et al., Circ. Shock, 42:39–43). Thus, XO blockade appears to be beneficial by three independent mechanisms: blockade of $O_2^-$ formation; inhibition of $O_2^-$ mediated pro-inflammatory gene expression; and preservation of the nucleotide pool available for ATP formation.

Accordingly, there is a clear need for compounds that inhibit the levels of xanthine oxidase in an animal and, accordingly, that are useful for treating or preventing an inflammation disease, a reperfusion disease, hyperuricemia, gout, tumor-lysis syndrome, or an inflammatory bowel disorder.

Citation of any reference in Section 2 of this application is not an admission that the reference is prior art to the application.

3. SUMMARY OF THE INVENTION

The invention encompasses compounds having the formula (Ia):

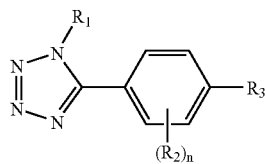

(Ia)

and a pharmaceutically acceptable salts and hydrates thereof, wherein:

$R_1$ is $CO_2R_4$;

each $R_2$ is independently -halo, $-NO_2$, $-CN$, $-OH$, $-N(R_5)(R_5)$, $-OR_5$, $-C(O)R_5$, $-OC(O)R_5$, $-C(O)NHC(O)R_5$, $-(C_1-C_{10})$alkyl, $-(C_2-C_{10})$alkenyl, $-(C_2-C_{10})$alkynyl, $-(C_3-C_{10})$cycloalkyl, $-(C_8-C_{14})$bicycloalkyl, $-(C_5-C_{10})$cycloalkenyl, $-(C_3-C_{10})$heterocycle, -phenyl, -naphthyl, -benzyl, $-CO_2R_5$, $-C(O)OCH(R_5)(R_5)$, $-NHC(O)R_5$, $-NHC(O)NHR_5$, $-C(O)NHR_5$, $-OC(O)R_5$, $-OC(O)OR_5$, $-SR_5$, $-S(O)R_5$, or $-S(O)_2R_5$;

$R_3$ is $-H$, -halo, $-NO_2$, $-CN$, $-OH$, $-N(R_5)(R_5)$, $-O(CH_2)_mR_5$, $-C(O)R_5$, $-C(O)N(R_5)(R_5)$, $-C(O)NH(CH_2)_m(R_5)$, $-OCF_3$, -benzyl, $-CO_2CH(R_5)(R_5)$, $-(C_1-C_{10})$alkyl, $-(C_2-C_{10})$alkenyl, $-(C_2-C_{10})$alkynyl, $-(C_3-C_{10})$cycloalkyl, $-(C_8-C_{14})$bicycloalkyl, $-(C_5-C_{10})$cycloalkenyl, -naphthyl, $-(C_3-C_{10})$heterocycle, $-CO_2(CH_2)_mR_5$, $-NHC(O)R_5$, $-N(R_5)C(O)R_5$, $-NHC(O)NHR_5$, $-OC(O)(CH_2)_mCHR_5R_5$, $-CO_2(CH_2)_mCHR_5R_5$, $-OC(O)OR_5$, $-SR_5$, $-S(O)R_5$, $-S(O)_2R_5$, $-S(O)_2NHR_5$, or

$R_4$ is $-(C_5)$heteroaryl, $-(C_6)$heteroaryl, phenyl, naphthyl, or benzyl;

each $R_5$ is independently $-H$, $-CF_3$, $-(C_1-C_{10})$alkyl, -benzyl, -adamantyl, -morpholinyl, -pyrrolidyl, -pyridyloxide, -pyrrolidinyldione, -piperdidyl, $-(C_2-C_{10})$alkenyl, $-(C_2-C_{10})$alkynyl, $-(C_3-C_{10})$cycloalkyl, $-(C_8-C_{14})$bicycloalkyl, $-(C_3-C_{10})$heterocycle, or

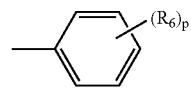

each $R_6$ is independently $-H$, -halo, $-NO_2$, $-CN$, $-OH$, $-CO_2H$, $-N((C_1-C_{10})$alkyl$(C_1-C_{10})$alkyl), $-O(C_1-C_{10})$alkyl, $-C(O)(C_1-C_{10})$alkyl, $-C(O)NH(CH_2)_m (C_1-C_{10})$alkyl, $-OCF_3$, -benzyl, $-CO_2(CH_2)_mCH((C_1-C_{10})$alkyl$(C_1-C_{10})$alkyl), $-C(O)H$, $-CO_2(C_1-C_{10})$alkyl, $-(C_1-C_{10})$alkyl, $-(C_2-C_{10})$alkenyl, $-(C_2-C_{10})$alkynyl, $-(C_3-C_{10})$cycloalkyl, $-(C_8-C_{14})$bicycloalkyl, $-(C_5-C_{10})$cycloalkenyl, $-(C_5)$heteroaryl, $-(C_6)$heteroaryl, -phenyl, naphthyl, $-(C_3-C_{10})$heterocycle, $-CO_2(CH_2)_m(C_1-C_{10})$alkyl, $-CO_2(CH_2)_mH$, $-NHC(O)(C_1-C_{10})$alkyl, $-NHC(O)NH(C_1-C_{10})$alkyl, $-OC(O)(C_1-C_{10})$alkyl, $-OC(O)O(C_1-C_{10})$alkyl, $-SO_2NHR_5$, or $-SO_2NH_2$;

n is an integer ranging from 0 to 4;

each m is independently an integer ranging from 0 to 8; and each p is independently an integer ranging from 0 to 5.

A compound of formula (Ia) or a pharmaceutically acceptable salt or hydrate thereof is useful for treating or preventing an inflammation disease, a reperfusion disease, hyperuricemia, gout, tumor-lysis syndrome, or an inflammatory bowel disorder in an animal.

The invention also relates to pharmaceutical compositions comprising an effective amount of a compound of formula (Ia) or a pharmaceutically acceptable salt or hydrate thereof; and a pharmaceutically acceptable carrier or vehicle. The compositions are useful for treating or preventing an inflammation disease, a reperfusion disease, hyperuricemia, gout, tumor-lysis syndrome, or an inflammatory bowel disorder.

The invention further relates to methods for treating or preventing an inflammation disease in an animal comprising administering to an animal in need thereof an effective amount of a compound of formula (Ib):

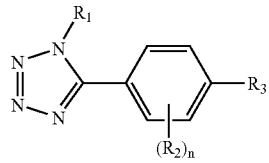

(Ib)

or a pharmaceutically acceptable salt or hydrate thereof, wherein:

$R_1$ is $-H$, $-CO_2R_4$, $-C(O)R_5$, or $-C(O)N(R_5)(R_5)$;

each $R_2$ is independently -halo, $-NO_2$, $-CN$, $-OH$, $-N(R_5)(R_5)$, $-OR_5$, $-C(O)R_5$, $-OC(O)R_5$, $-CONHC(O)R_5$, $-(C_1-C_{10})$alkyl, $-(C_2-C_{10})$alkenyl, $-(C_2-C_{10})$alkynyl, $-(C_3-C_{10})$cycloalkyl, $-(C_8-C_{14})$bicycloalkyl, $-(C_5-C_{10})$cycloalkenyl, $-(C_3-C_7)$heterocycle, $-(C_5)$heteroaryl, $-(C_6)$heteroaryl, phenyl, -naphthyl, -benzyl, $-CO_2R_5$, $-C(O)OCH(R_5)(R_5)$, $-NHC(O)R_5$, $-NHC(O)NHR_5$, $-C(O)NHR_5$, $-OC(O)R_5$, $-OC(O)OR_5$, $-SR_5$, $-S(O)R_5$, or $-S(O)_2R_5$;

$R_3$ is $-H$, -halo, $-NO_2$, $-CN$, $-OH$, $-N(R_5)(R_5)$, $-O(CH_2)_mR_5$, $-C(O)R_5$, $-C(O)NR_5R_5$, $-C(O)NH(CH_2)_m(R_5)$, $-OCF_3$, -benzyl, $-CO_2CH(R_5)(R_5)$, $-(C_1-C_{10})$alkyl, $-(C_2-C_{10})$alkenyl, $-(C_2-C_{10})$alkynyl, $-(C_3-C_{10})$cycloalkyl, $-(C_8-C_{14})$bicycloalkyl, $-(C_5-C_{10})$cycloalkenyl, $-(C_5)$heteroaryl, $-(C_6)$heteroaryl, -naphthyl, $-(C_3-C_{10})$heterocycle, $-CO_2(CH_2)_mR_5$, $-NHC(O)R_5$, $-NHC(O)R_5$, $-NHC(O)NHR_5$, $-OC(O)(CH_2)_mCHR_5R_5$, $-CO_2(CH_2)_mCHR_5R_5$, $-OC(O)OR_5$, $-SR_5$, $-S(O)R_5$, $-S(O)_2R_5$, $-S(O)_2NHR_5$, or

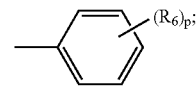

$R_4$ is $-CF_3$, $-(C_1-C_{10})$alkyl, -benzyl, -adamantyl, -morpholinyl, -pyrrolidyl, -pyridyloxide, -pyrrolidinyldione, -piperdidyl, $-(C_5)$heteroaryl, $-(C_6)$heteroaryl, $-(C_2-C_{10})$alkenyl, $-(C_2-C_{10})$alkynyl, $-(C_3-C_{10})$cycloalkyl, $-(C_8-C_{14})$bicycloalkyl, $-(C_3-C_{10})$heterocycle, or

each $R_5$ is independently H or $R_4$;

each $R_6$ is independently -halo, $-NO_2$, $-CN$, $-OH$, $-CO_2H$, $-N(C_1-C_{10})alkyl(C_1-C_{10})alkyl$, $-O(C_1-C_{10})alkyl$, $-C(O)(C_1-C_{10})alkyl$, $-C(O)NH(CH_2)_m(C_1-C_{10})alkyl$, $-OCF_3$, -benzyl, $-CO_2(CH_2)_mCH((C_1-C_{10})alkyl(C_1-C_{10})alkyl)$, $-C(O)H$, $-CO_2(C_1-C_{10})alkyl$, $-(C_1-C_{10})alkyl$, $-(C_2-C_{10})alkenyl$, $-(C_2-C_{10})alkynyl$, $-(C_3-C_{10})cycloalkyl$, $-(C_8-C_{14})bicycloalkyl$, $-(C_5-C_{10})cycloalkenyl$, $-(C_5)heteroaryl$, $-(C_6)heteroaryl$, -phenyl, naphthyl, $-(C_3-C_{10})heterocycle$, $-CO_2(CH_2)_m(C_1-C_{10})alkyl$, $-CO_2(CH_2)_mH$, $-NHC(O)(C_1-C_{10})alkyl$, $-NHC(O)NH(C_1-C_{10})alkyl$, $-OC(O)(C_1-C_{10})alkyl$, $-OC(O)O(C_1-C_{10})alkyl$, or $-SO_2NH_2$;

n is an integer ranging from 0 to 4;

each m is independently an integer ranging from 0 to 8; and each p is independently an integer ranging from 0 to 5.

The invention further relates to methods for treating or preventing a reperfusion disease, comprising administering to an animal in need thereof an effective amount of a compound of formula (Ib) or a pharmaceutically acceptable salt or hydrate thereof.

The invention further relates to methods for treating or preventing hyperuricemia or gout, comprising administering to an animal in need thereof an effective amount of a compound of formula (Ib) or a pharmaceutically acceptable salt or hydrate thereof.

The invention further relates to methods for treating or preventing tumor-lysis syndrome, comprising administering to an animal in need thereof an effective amount of a compound of formula (Ib) or a pharmaceutically acceptable salt or hydrate thereof.

The invention further relates to methods for treating or preventing an inflammatory bowel disorder, comprising administering to an animal in need thereof an effective amount of a compound of formula (Ib) or a pharmaceutically acceptable salt or hydrate thereof.

The invention further relates to methods for inhibiting xanthine oxidase activity, comprising administering to an animal in need thereof an effective amount of a compound of formula (Ib) or a pharmaceutically acceptable salt or hydrate thereof.

The invention also relates to kits comprising a container containing a compound of formula (Ia) or (Ib) or a pharmaceutically acceptable salt or hydrate thereof (each being a "5-Aryltetrazole Compound").

The invention can be understood more fully by reference to the following detailed description and illustrative examples, which are intended to exemplify non-limiting embodiments of the invention.

4. DETAILED DESCRIPTION OF THE INVENTION

4.1. Definitions

As used herein, the term "$-(C_1-C_{10})alkyl$" means a saturated straight chain or branched non-cyclic hydrocarbon having from 1 to 10 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, -2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like.

As used herein, the term "$-(C_2-C_{10})alkenyl$" means a straight chain or branched non-cyclic hydrocarbon having from 2 to 10 carbon atoms and including at least one carbon-carbon double bond. Representative straight chain and branched $(C_2-C_{10})alkenyls$ include -vinyl, -allyl, -1-butenyl, -2-butenyl, -isobutylenyl, -1-pentenyl, -2-pentenyl, -3-methyl-1-butenyl, -2-methyl-2-butenyl, 2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

As used herein, the term "$-(C_2-C_{10})alkynyl$" means a straight chain or branched non-cyclic hydrocarbon having from 2 to 10 carbon atoms and including at lease one carbon-carbon triple bond. Representative straight chain and branched $-(C_2-C_{10})alkynyls$ include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl and the like.

As used herein, the term "$-(C_3-C_{10})cycloalkyl$" means a saturated cyclic hydrocarbon having from 3 to 10 carbon atoms. Representative $(C_3-C_{10})cycloalkyls$ include -cyclopropyl, -cyclobutyl, -cyclopentyl, -cyclohexyl, -cycloheptyl, -cyclooctyl, -cyclononyl, and -cyclodecyl.

As used herein, the term "$-(C_8-C_{14})bicycloalkyl$" means a bi-cyclic hydrocarbon ring system having from 8 to 14 carbon atoms and at least one saturated cyclic alkyl ring. Representative $-(C_8-C_{14})bicyclocycloalkyls$ include -indanyl, -1,2,3,4-tetrahydronaphthyl, -5,6,7,8-tetrahydronaphthyl, -perhydronaphthyl and the like.

As used herein, the term "$-(C_5-C_{10})cycloalkenyl$" means a cyclic non-aromatic hydrocarbon having at least one carbon-carbon double bond in the cyclic system and from 5 to 10 carbon atoms. Representative $(C_5-C_{10})cycloalkenyls$ include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl and the like.

As used herein, the term "$-(C_3-C_{10})heterocycle$" or "$-(C_3-C_{10})heterocyclo$" means a 3- to 10-membered monocyclic heterocyclic ring which is either saturated, unsaturated non-aromatic, or aromatic. A 3-membered $-(C_3-C_7)heterocycle$ can contain up to 3 heteroatoms, and a 4- to 10-membered $-(C_3-C_{10})heterocycle$ can contain up to 4 heteroatoms. Each heteroatom is independently selected from nitrogen, which can be quaternized; oxygen; and sulfur, including sulfoxide and sulfone. The $-(C_3-C_{10})$ heterocycle may be attached via any heteroatom or carbon atom. Representative —($C_3$–$C_{10}$)heterocycles include pyridyl, furyl, thiophenyl, pyrrolyl, oxazolyl, imidazolyl, thiazolyl, isoxazolyl, pyrazolyl, isothiazolyl, pyridazinyl, pyrimidinyl, pyrazinyl, triazinyl, morpholinyl, pyrrolidinonyl, pyrrolidinyl, piperidinyl, piperazinyl, benzo[1,3]dioxolyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group or the hydrogen on an oxygen may be substituted with a methoxymethyl.

As used herein, the term "—($C_5$)heteroaryl" means an aromatic heterocycle ring of 5 members, wherein at least one carbon atom of the ring is replaced with a heteroatom such as, for example, nitrogen. Representative —($C_5$)heteroaryls include furyl, thienyl, pyrrolyl, oxazolyl, imidazolyl, thiazolyl, isoxazolyl, pyrazolyl, isothiazolyl, pyrazinyl, triazolyl, thiadiazolyl, and the like.

As used herein, the term "—($C_6$)heteroaryl" means an aromatic heterocycle ring of 6 members, wherein at least one carbon atom of the ring is replaced with a heteroatom such as, for example, nitrogen. One of the —($C_6$)heteroaryl's rings contain at least one carbon atom. Representative ($C_6$)heteroaryls include pyridyl, pyridazinyl, pyrazinyl, triazinyl, tetrazinyl and the like.

As used herein, the term "-Halogen" or "-Halo" means —F, —Cl, —Br or —I.

As used herein, the term "animal," includes, but is not limited to, a cow, monkey, horse, sheep, pig, chicken, turkey, quail, cat, dog, mouse, rat, rabbit, guinea pig and human.

As used herein, the term "adamantyl" includes 1-adamantyl, 2-adamantyl, and 3-adamantyl.

As used herein, the term "naphthyl" includes 1-naphthyl and 2-naphthyl.

As used herein, the term "morpholinyl" includes N-morpholinyl, 2-morpholinyl, and 3-morpholinyl.

As used herein, the term "pyrridyloxide" includes 2-pyrridyloxide, 3-pyrridyloxide, and 4-pyrridyloxide.

As used herein, the term "pyrrolidinyldione" includes N-pyrrolidinyl-2,3-dione, N-pyrrolidinyl-2,4-dione, N-pyrrolidinyl-2,5-dione, N-pyrrolidinyl-3,5-dione, N-pyrrolidinyl-3,4-dione, 2-pyrrolidinyl-3,4-dione, or 3-pyrrolidinyldione-2,4-dione, and 3-pyrrolidinyl-2,5-dione.

As used herein, the term "piperdinyl" includes N-piperdinyl, 2-piperdinyl, and 3-piperdinyl.

As used herein, the term "pharmaceutically acceptable salt," is a salt formed from an acid and a basic nitrogen group of one of the 5-Aryltetrazole Compounds. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a 5-Aryltetrazole Compound having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

As used herein, the term "pharmaceutically acceptable hydrate," is a hydrate formed from the association of one or more water molecules of one of the 5-Aryltetrazole Compounds. The term hydrate includes a mono-hydrate, dihydrate, trihydrate, tetrahydrate, and the like.

4.2. Compounds of Formula (Ia)

As stated above, the invention encompasses compounds of formula (Ia):

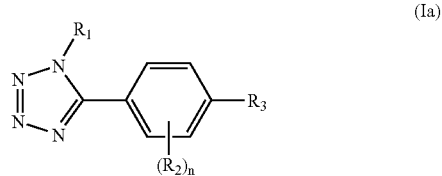

(Ia)

and pharmaceutically acceptable salts and hydrates thereof, wherein:

$R_1$ is $CO_2R_4$;

each $R_2$ is independently -halo, —$NO_2$, —CN, —OH, —N($R_5$)($R_5$), —$OR_5$, —C(O)$R_5$, —OC(O)$R_5$, —C(O)NHC(O)$R_5$, —($C_1$–$C_{10}$)alkyl, —($C_2$–$C_{10}$)alkenyl, —($C_2$–$C_{10}$)alkynyl, —($C_3$–$C_{10}$)cycloalkyl, —($C_8$–$C_{14}$)bicycloalkyl, —($C_5$–$C_{10}$)cycloalkenyl, —($C_3$–$C_{10}$)heterocycle, -phenyl, -naphthyl, -benzyl, —$CO_2R_5$, —C(O)OCH($R_5$)($R_5$), —NHC(O)$R_5$, —NHC(O)NH$R_5$, —C(O)NH$R_5$, —OC(O)$R_5$, —OC(O)O$R_5$, —S$R_5$, —S(O)$R_5$, or —S(O)$_2R_5$;

$R_3$ is —H, -halo, —$NO_2$, —CN, —OH, —N($R_5$)($R_5$), —O($CH_2$)$_mR_5$, —C(O)$R_5$, —C(O)NR$_5R_5$, —C(O)NH($CH_2$)$_m$($R_5$), —$OCF_3$, -benzyl, —$CO_2$CH($R_5$)($R_5$), —($C_1$–$C_{10}$)alkyl, —($C_2$–$C_{10}$)alkenyl, —($C_2$–$C_{10}$)alkynyl, —($C_3$–$C_{10}$)cycloalkyl, —($C_8$–$C_{14}$)bicycloalkyl, —($C_5$–$C_{10}$)cycloalkenyl, -naphthyl, —($C_3$–$C_{10}$)heterocycle, —$CO_2$($CH_2$)$_mR_5$, —NHC(O)$R_5$, —N($R_5$)C(O)$R_5$, —NHC(O)NH$R_5$, —OC(O)($CH_2$)$_m$CHR$_5R_5$, —$CO_2$($CH_2$)$_m$CHR$_5R_5$, —OC(O)O$R_5$, —S$R_5$, —S(O)$R_5$, —S(O)$_2R_5$, —S(O)$_2$NH$R_5$, or —⟨phenyl⟩($R_6$)$_p$;

$R_4$ is —($C_5$)heteroaryl, —($C_6$)heteroaryl, phenyl, naphthyl, or benzyl;

each $R_5$ is independently —H, —$CF_3$, —($C_1$–$C_{10}$)alkyl, -benzyl, -adamantyl, -morpholinyl, -pyrrolidyl, -pyrridyloxide, -pyrrolidinyldione, -piperdidyl, —($C_2$–$C_{10}$)alkenyl, —($C_2$–$C_{10}$)alkynyl, —($C_3$–$C_{10}$)cycloalkyl, —($C_8$–$C_{14}$)bicycloalkyl, —($C_3$–$C_{10}$)heterocycle, or

each $R_6$ is independently —H, -halo, —$NO_2$, —CN, —OH, —$CO_2H$, —N(($C_1$–$C_{10}$)alkyl($C_1$–$C_{10}$)alkyl), —O($C_1$–$C_{10}$)alkyl, —C(O)($C_1$–$C_{10}$)alkyl, —C(O)NH$(CH_2)_m$ ($C_1$–$C_{10}$)alkyl, —$OCF_3$, -benzyl, —$CO_2(CH_2)_m$CH(($C_1$–$C_{10}$)alkyl($C_1$–$C_{10}$)alkyl), —C(O)H, —$CO_2$($C_1$–$C_{10}$)alkyl, —($C_1$–$C_{10}$)alkyl, —($C_2$–$C_{10}$)alkenyl, —($C_2$–$C_{10}$)alkynyl, —($C_3$–$C_{10}$)cycloalkyl, —($C_8$–$C_{14}$)bicycloalkyl, —($C_5$–$C_{10}$)cycloalkenyl, —($C_5$)heteroaryl, —($C_6$)heteroaryl, -phenyl, naphthyl, —($C_3$–$C_{10}$)heterocycle, —$CO_2(CH_2)_m$($C_1$–$C_{10}$)alkyl, —$CO_2(CH_2)_m$H, —NHC(O)($C_1$–$C_{10}$)alkyl, —NHC(O)NH($C_1$–$C_{10}$)alkyl, —OC(O)($C_1$–$C_{10}$)alkyl, —OC(O)O($C_1$–$C_{10}$)alkyl, —$SO_2NHR_5$, and —$SO_2NH_2$;

n is an integer ranging from 0 to 4;

each m is independently an integer ranging from 0 to 8; and each p is independently an integer ranging from 0 to 5.

In one embodiment n is 0.

In another embodiment n is 0 and $R_3$ is -halo.

In another embodiment n is 0 and $R_3$ is —C(O)$R_5$.

In another embodiment n is 0 and $R_3$ is —C(O)NHC(O)$R_5$.

In another embodiment n is 0 and $R_3$ is —C(O)N($R_5$)($R_5$).

In another embodiment n is 0 and $R_3$ is —$CO_2(CH_2)_m$($R_5$).

In another embodiment n is 0 and $R_3$ is —H.

In another embodiment n is 0 and $R_3$ is —NHC(O)N($R_5$)($R_5$).

In another embodiment n is 0 and $R_3$ is —C(O)NH$R_5$.

In another embodiment n is 0; $R_3$ is —C(O)NH$R_5$; and $R_5$ is

In another embodiment n is 0; $R_3$ is —C(O)NH$R_5$; $R_5$ is

and p is an integer from 1 to 3.

In another embodiment n is 0; $R_3$ is —C(O)NH$R_5$; $R_5$ is

and p is 1 or 2.

In another embodiment n is 0; $R_3$ is —C(O)NH$R_5$; $R_5$ is

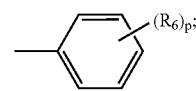

p is 1; and $R_6$ is in the para position.

In another embodiment n is 0; $R_3$ is —C(O)NH$R_5$; $R_5$ is

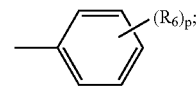

p is 1; and $R_6$ is in a meta position.

In another embodiment n is 0; $R_3$ is —C(O)NH$R_5$; $R_5$ is

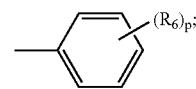

p is 1; and $R_6$ is in an ortho position.

In another embodiment n is 0; $R_3$ is —C(O)NH$R_5$; $R_5$ is

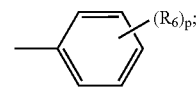

and each $R_6$ is independently -halo.

In another embodiment n is 0; $R_3$ is —C(O)NH$R_5$; $R_5$ is

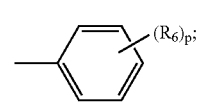

p is 2; and each $R_6$ is independently -halo.

In another embodiment n is 0; $R_3$ is —C(O)NH$R_5$; $R_5$ is

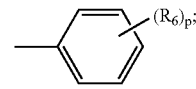

p is 2; each $R_6$ is independently halo; and one $R_6$ is in the para position and the other $R_6$ is in a meta position.

In another embodiment n is 0; $R_3$ is —C(O)NH$R_5$; $R_5$ is

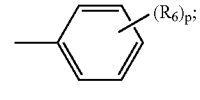

p is 2; each $R_6$ is independently halo; and one $R_6$ is in the para position and the other $R_6$ is in an ortho position.

In another embodiment n is 0; R₃ is —C(O)NHR₅; R₅ is

p is 2; each R₆ is independently halo; and one R₆ is in an ortho position and the other R₆ is in a meta position.

In another embodiment n is 0; R₃ is —C(O)NHR₅; R₅ is

p is 2; each R₆ is independently halo; and each R₆ in an ortho position.

In another embodiment n is 0; R₃ is —C(O)NHR₅; R₅ is

p is 2; each R₆ is independently halo; and each R₆ is in a meta position.

The invention also encompasses pharmaceutical compositions comprising an effective amount of a compound of formula (Ia) or a pharmaceutically acceptable salt or hydrate of the compound of formula (Ia) and a pharmaceutically acceptable carrier or excipient.

Illustrative subclasses of formula (Ia) have the following formulas, wherein R₄ is —(C₅)heteroaryl, —(C₆)heteroaryl, phenyl, naphthyl, or benzyl:

Formula AA
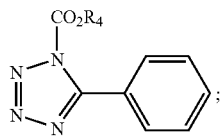

Formula AB
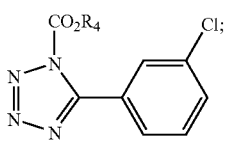

Formula AC
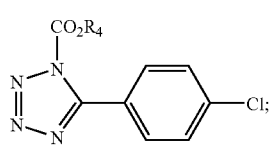

Formula AD
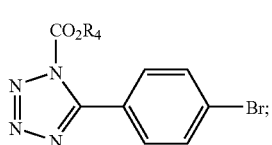

Formula AE
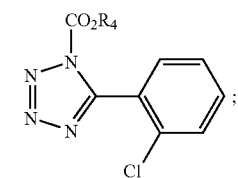

Formula AF
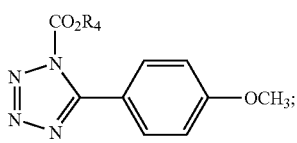

Formula AG
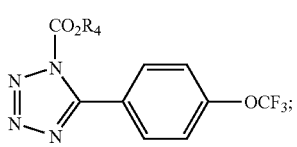

Formula AH
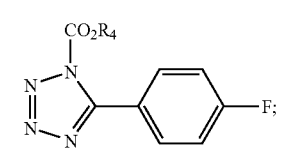

Formula AI
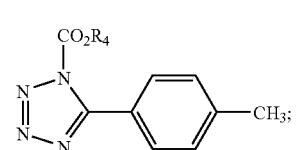

Formula AJ
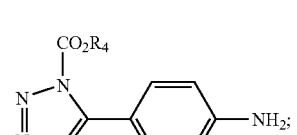

Formula AK
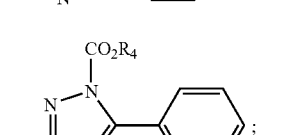

Formula AL
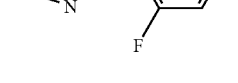

Formula AM
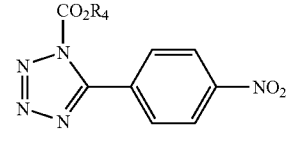

Formula AN
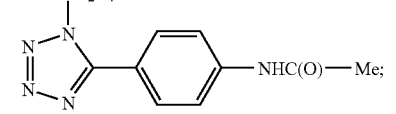

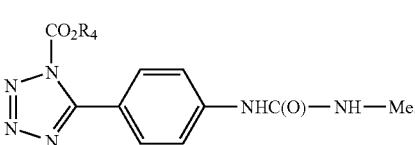

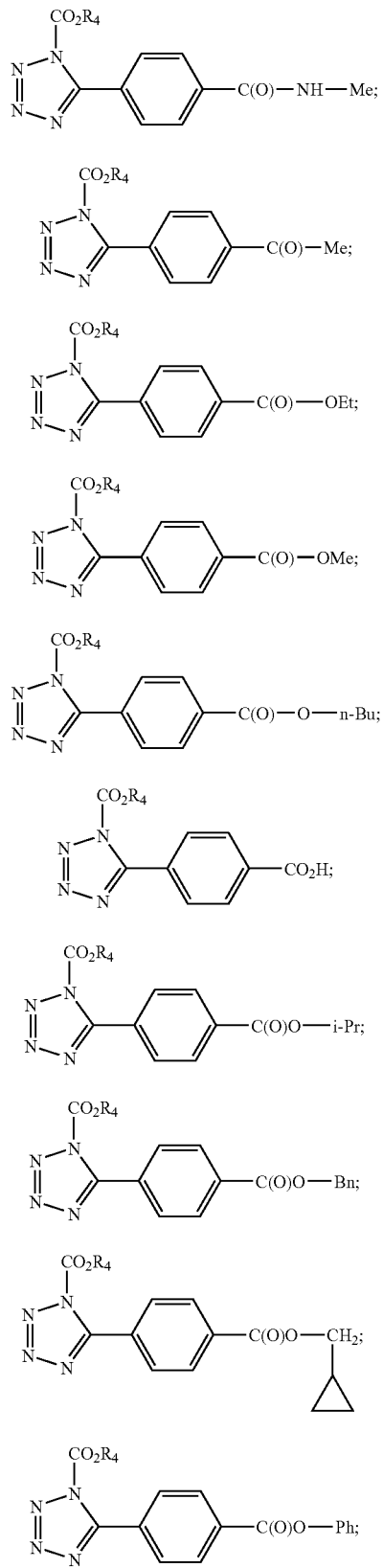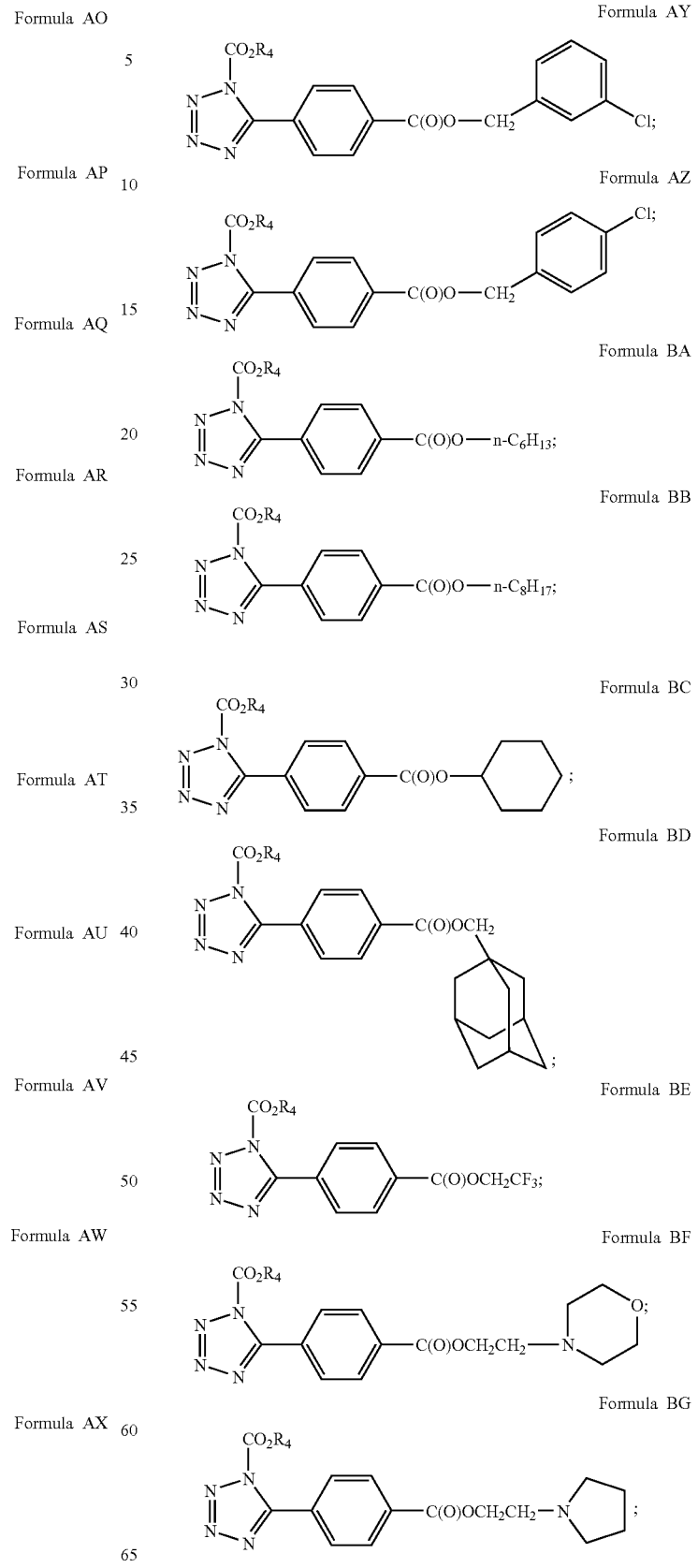

-continued

Formula BH, BI, BJ, BK, BL, BM, BN, BO, BP, BQ, BR, BS, BT, BU, BV, BW, BX, BY (chemical structures)

-continued

Formula BZ

Formula CA

Formula CB

Formula CC

Formula CD

Formula CE

Formula CF

Formula CG

-continued

Formula CH

Formula CI

Formula CJ

Formula CK

Formula CL

Formula CM

Formula CN

Formula CO

Formula CP

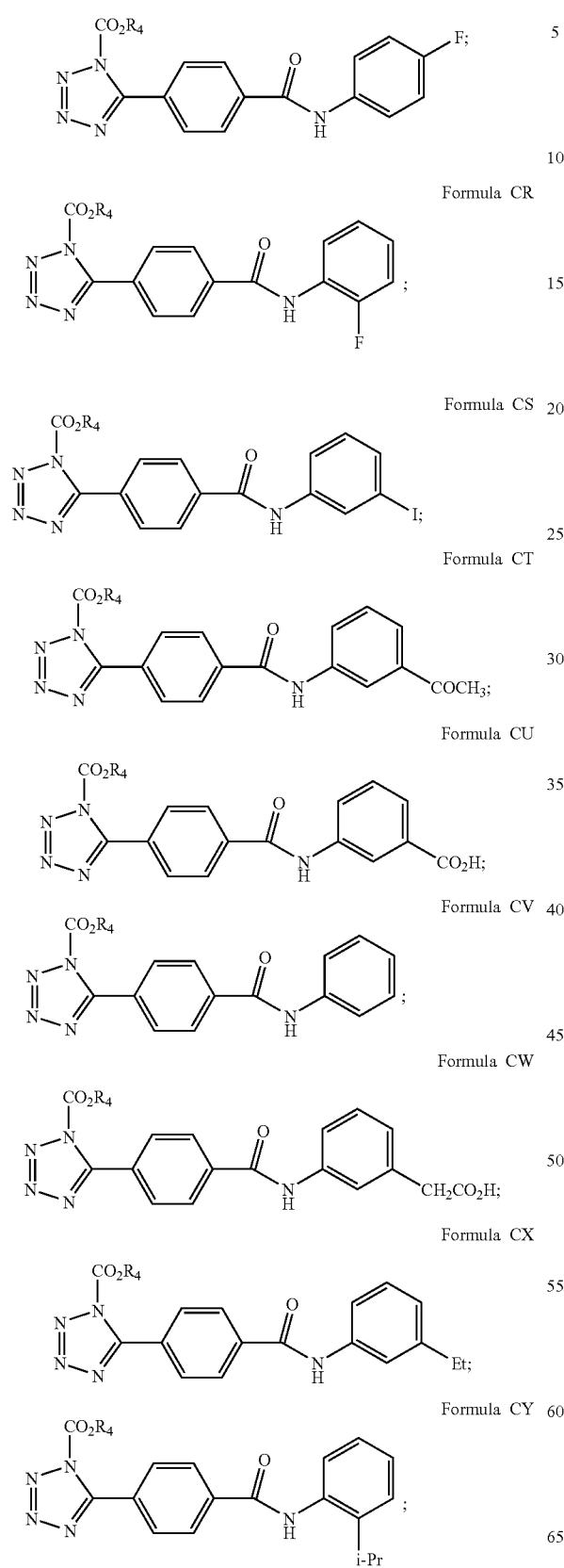

-continued
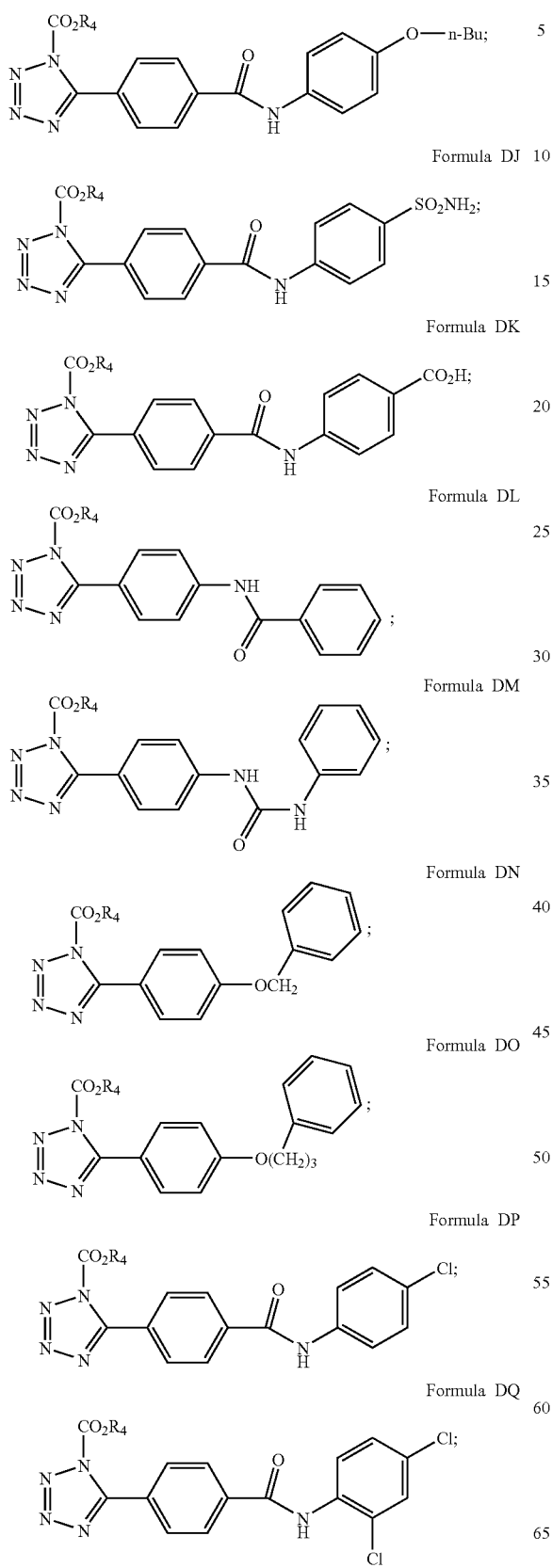
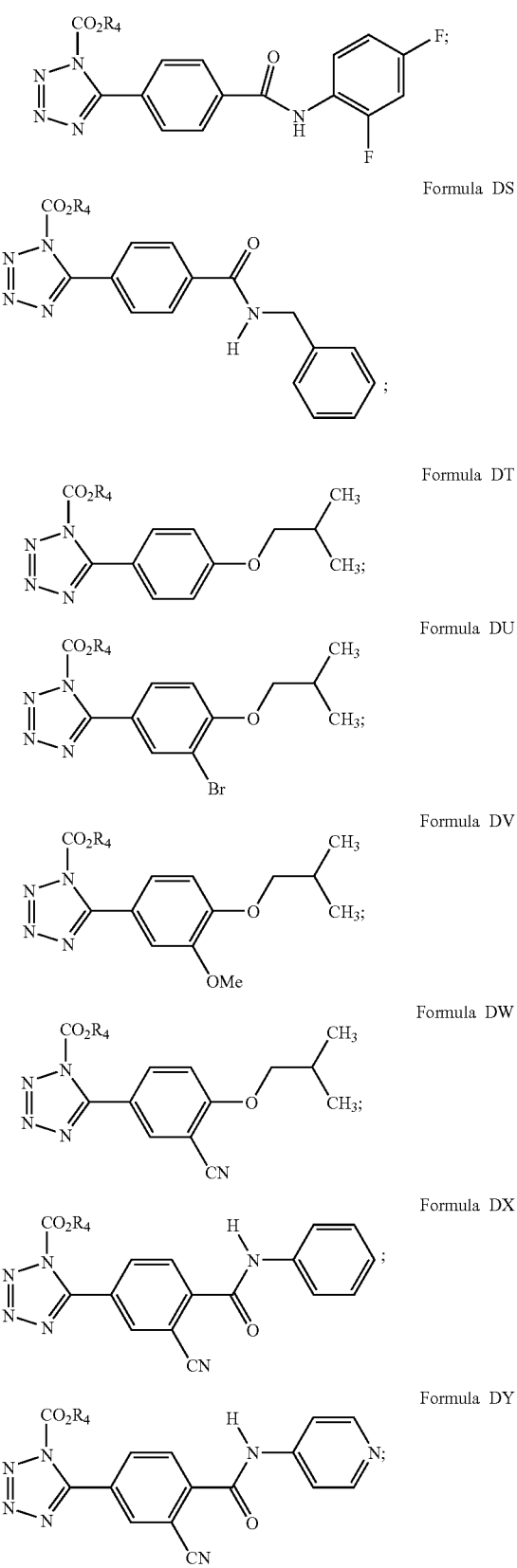

4.3. Compounds of Formula (Ib)

The invention further relates to methods for treating or preventing an inflammation disease, a reperfusion disease, hyperuricemia, gout, tumor-lysis syndrome, or an inflammatory bowel disorder, comprising administering to an animal in need thereof an effective amount of a compound of formula (Ib):

$$\text{(Ib)}$$

or a pharmaceutically acceptable salt or hydrate thereof, wherein:

$R_1$ is —H, —$CO_2R_4$; —$C(O)R_5$, or —$C(O)N(R_5)(R_5)$;

each $R_2$ is independently -halo, —$NO_2$, —CN, —OH, —$N(R_5)(R_5)$, —$OR_5$, —$C(O)R_5$, —$C(O)NHC(O)R_5$, —$OC(O)R_5$, —$(C_1–C_{10})$alkyl, —$(C_2–C_{10})$alkenyl, —$(C_2–C_{10})$alkynyl, —$(C_3–C_{10})$cycloalkyl, —$(C_8–C_{14})$bicycloalkyl, —$(C_5–C_{10})$cycloalkenyl, —$(C_3–C_7)$heterocycle, —$(C_5)$heteroaryl, —$(C_6)$heteroaryl, phenyl, -naphthyl, -benzyl, —$CO_2R_5$, —$C(O)OCH(R_5)(R_5)$, —$NHC(O)R_5$, —$NHC(O)NHR_5$, —$C(O)NHR_5$, —$OC(O)R_5$, —$OC(O)OR_5$, —$SR_5$, —$S(O)R_5$, or —$S(O)_2R_5$;

$R_3$ is —H, -halo, —$NO_2$, —CN, —OH, —$N(R_5)(R_5)$, —$O(CH_2)_mR_5$, —$C(O)R_5$, —$C(O)N(R_5)(R_5)$, —$C(O)NH(CH_2)_m(R_5)$, —$OCF_3$, -benzyl, —$CO_2CH(R_5)(R_5)$, —$(C_1–C_{10})$alkyl, —$(C_2–C_{10})$alkenyl, —$(C_2–C_{10})$alkynyl, —$(C_3–C_{10})$cycloalkyl, —$(C_8–C_{14})$bicycloalkyl, —$(C_5–C_{10})$cycloalkenyl, —$(C_5)$heteroaryl, —$(C_6)$heteroaryl, -naphthyl, —$(C_3–C_{10})$heterocycle, —$CO_2(CH_2)_mR_5$, —$NHC(O)R_5$, —$NHC(O)R_5$, —$NHC(O)NHR_5$, —$OC(O)(CH_2)_mCHR_5R_5$, —$CO_2(CH_2)_mCHR_5R_5$, —$OC(O)OR_5$, —$SR_5$, —$S(O)R_5$, —$S(O)_2R_5$, —$S(O)_2NHR_5$, or $$\text{—}\diagdown\!\!\!\diagup\text{(R}_6)_p;$$

each $R_4$ is independently —$CF_3$, —$(C_1–C_{10})$alkyl, -benzyl, -adamantyl, -morpholinyl, -pyrrolidyl, -pyrridyloxide, -pyrrolidinyldione, -piperdinyl, —$(C_5)$heteroaryl, —$(C_6)$heteroaryl, —$(C_2–C_{10})$alkenyl, —$(C_2–C_{10})$alkynyl, —$(C_3–C_{10})$cycloalkyl, —$(C_8–C_{14})$bicycloalkyl, —$(C_3–C_{10})$heterocycle, or $$\text{—}\diagdown\!\!\!\diagup\text{(R}_6)_p;$$

each $R_5$ is independently —H or —$R_4$;

each $R_6$ is independently -halo, —$NO_2$, —CN, —OH, —$CO_2H$, —$N(C_1–C_{10})$alkyl$(C_1–C_{10})$alkyl, —$O(C_1–C_{10})$alkyl, —$C(O)(C_1–C_{10})$alkyl, —$C(O)NH(CH_2)_m(C_1–C_{10})$alkyl, —$OCF_3$, -benzyl, —$CO_2(CH_2)_mCH((C_1–C_{10})$alkyl$(C_1–C_{10})$alkyl), —$C(O)H$, —$CO_2(C_1–C_{10})$alkyl, —$(C_1–C_{10})$alkyl, —$(C_2–C_{10})$alkenyl, —$(C_2–C_{10})$alkynyl, —$(C_3-C_{10})$cycloalkyl, —$(C_8-C_{14})$bicycloalkyl, —$(C_5-C_{10})$cycloalkenyl, —$(C_5)$heteroaryl, —$(C_6)$heteroaryl, -phenyl, naphthyl, —$(C_3-C_{10})$heterocycle, —$CO_2(CH_2)_m(C_1-C_{10})$alkyl, —$CO_2(CH_2)_mH$, —$NHC(O)(C_1-C_{10})$alkyl, —$NHC(O)NH(C_1-C_{10})$alkyl, —$OC(O)(C_1-C_{10})$alkyl, —$OC(O)O(C_1-C_{10})$alkyl, or —$SO_2NH_2$;

n is an integer ranging from 0 to 4;

each m is independently an integer ranging from 0 to 8; and each p is independently an integer ranging from 0 to 5.

In one embodiment $R_1$ is —H.

In another embodiment $R_1$ is —H; n is 0; and $R_3$ is -halo.

In another embodiment $R_1$ is —H; n is 0; and $R_3$ is —$C(O)R_5$.

In another embodiment $R_1$ is —H; n is 0; and $R_3$ is —$C(O)NHC(O)R_5$.

In another embodiment $R_1$ is —H; n is 0; and $R_3$ is —$C(O)N(R_5)(R_5)$.

In another embodiment $R_1$ is —H; n is 0; and $R_3$ is —H.

In another embodiment $R_1$ is —H; n is 0; and $R_3$ is —$CO_2(CH_2)_m(R_5)$.

In another embodiment $R_1$ is —H; n is 0; and $R_3$ is —$NHC(O)N(R_5)(R_5)$.

In another embodiment $R_1$ is —H; n is 0; and $R_3$ is —$C(O)NHR_5$.

In another embodiment $R_1$ is —H; n is 0; $R_3$ is —$C(O)NHR_5$; and $R_5$ is

In another embodiment $R_1$ is —H; n is 0; $R_3$ is —$C(O)NHR_5$; $R_5$ is

and p is an integer from 1 to 3.

In another embodiment $R_1$ is —H; n is 0; $R_3$ is —$C(O)NHR_5$; $R_5$ is

and p is 1 or 2.

In another embodiment $R_1$ is —H; n is 0; $R_3$ is —$C(O)NHR_5$, $R_5$ is

p is 1; and $R_6$ is halo and is in the para position.

In another embodiment $R_1$ is —H; n is 0; $R_3$ is —$C(O)NHR_5$; $R_5$ is

p is 1; and $R_6$ is halo and is in a meta position.

In another embodiment $R_1$ is —H; n is 0; $R_3$ is —$C(O)NHR_5$, $R_5$ is

p is 1; and $R_6$ is halo and is in an ortho position.

In another embodiment $R_1$ is —H; n is 0; $R_3$ is —$C(O)NHR_5$, $R_5$ is

p is 2; and each $R_6$ is independently -halo.

In another embodiment $R_1$ is —H; n is 0; $R_3$ is —$C(O)NHR_5$, $R_5$ is

p is 2; each $R_6$ is independently -halo; and one $R_6$ is in the para position and the other $R_6$ is in a meta position.

In another embodiment $R_1$ is —H; n is 0; $R_3$ is —$C(O)NHR_5$; $R_5$ is

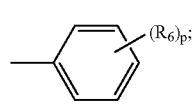

p is 2; each $R_6$ is independently -halo; and one $R_6$ is in the para position and the other $R_6$ is in an ortho position.

In another embodiment $R_1$ is —H; n is 0; $R_3$ is —$C(O)NHR_5$; $R_5$ is

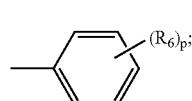

p is 2; and one $R_6$ is in an ortho position and the other $R_6$ is in a meta position.

In another embodiment, $R_1$ is —$CO_2R_4$.

In another embodiment $R_1$ is —$CO_2R_4$ and n is 0.

In another embodiment $R_1$ is —$CO_2R_4$; n is 0; and $R_3$ is -halo.

In another embodiment $R_1$ is $-CO_2R_4$; n is 0; and $R_3$ is $-C(O)R_5$.

In another embodiment $R_1$ is $-CO_2R_4$; n is 0; and $R_3$ is $-C(O)NHC(O)R_5$.

In another embodiment $R_1$ is $-CO_2R_4$; n is 0; and $R_3$ is $-H$.

In another embodiment $R_1$ is $-CO_2R_4$; n is 0; and $R_3$ is $-CO_2(CH_2)_m(R_5)$.

In another embodiment $R_1$ is $-CO_2R_4$; n is 0; and $R_3$ is $-NHC(O)N(R_5)(R_5)$.

In another embodiment $R_1$ is $-CO_2R_4$; n is 0; and $R_3$ is $-C(O)N(R_5)(R_5)$.

In another embodiment $R_1$ is $-CO_2R_4$; n is 0; and $R_3$ is $-C(O)NHR_5$.

In another embodiment $R_1$ is $-CO_2R_4$; n is 0; $R_3$ is $-C(O)NHR_5$; and $R_5$ is

and p is an integer from 1 to 3.

In another embodiment $R_1$ is $-CO_2R_4$; n is 0; $R_3$ is $-C(O)NHR_5$; $R_5$ is

and p is 1 or 2.

In another embodiment $R_1$ is $-CO_2R_4$; n is 0; $R_3$ is $-C(O)NHR_5$; $R_5$ is

p is 1; and $R_6$ is halo and is in the para position.

In another embodiment $R_1$ is $-CO_2R_4$; n is 0; $R_3$ is $-C(O)NHR_5$; $R_5$ is

p is 1, and $R_6$ is halo and is in a meta position.

In another embodiment $R_1$ is $-CO_2R_4$; n is 0; $R_3$ is $-C(O)NHR_5$; $R_5$ is

p is 1, and $R_6$ is halo and is in an ortho position.

In another embodiment $R_1$ is $-CO_2R_4$; n is 0; $R_3$ is $-C(O)NHR_5$; $R_5$ is

p is 2; and each $R_6$ is independently -halo.

In another embodiment $R_1$ is $-CO_2R_4$; n is 0; $R_3$ is $-C(O)NHR_5$; $R_5$ is

p is 2; each $R_6$ is independently halo; and one $R_6$ is in the para position and the other $R_6$ is in a meta position.

In another embodiment $R_1$ is $-CO_2R_4$; n is 0; $R_3$ is $-C(O)NHR_5$, $R_5$ is

p is 2; each $R_6$ is independently halo; and one $R_6$ is in the para position and the other $R_6$ is in an ortho position.

In another embodiment $R_1$ is $-CO_2R_4$; n is 0; $R_3$ is $-C(O)NHR_5$, $R_5$ is

p is 2; each $R_6$ is independently halo; and one $R_6$ is in the ortho position and the other $R_6$ is in a meta position.

In another embodiment, $R_1$ is $-C(O)R_5$.

In another embodiment $R_1$ is $-C(O)R_5$; n is 0; and $R_3$ is -halo.

In another embodiment $R_1$ is $-C(O)R_5$; n is 0; and $R_3$ is $-C(O)R_5$.

In another embodiment $R_1$ is $-C(O)R_5$; n is 0; and $R_3$ is $-C(O)NHC(O)R_5$.

In another embodiment $R_1$ is $-C(O)R_5$; n is 0; and $R_3$ is $-H$.

In another embodiment $R_1$ is $-C(O)R_5$; n is 0; and $R_3$ is $-CO_2(CH_2)_m(R_5)$.

In another embodiment $R_1$ is $-C(O)R_5$; n is 0; and $R_3$ is $-NHC(O)N(R_5)(R_5)$.

In another embodiment $R_1$ is $-C(O)R_5$; n is 0; and $R_3$ is $C(O)N(R_5)(R_5)$.

In another embodiment $R_1$ is —C(O)$R_5$; n is 0; and $R_3$ is —C(O)NH$R_5$.

In another embodiment $R_1$ is —C(O)$R_5$; n is 0; $R_3$ is —C(O)NH$R_5$; and $R_5$ is

In another embodiment $R_1$ is —C(O)$R_5$; n is 0; $R_3$ is —C(O)NH$R_5$; $R_5$ is

and p is an integer from 1 to 3.

In another embodiment $R_1$ is —C(O)$R_5$; n is 0; $R_3$ is —C(O)NH$R_5$; $R_5$ is

and p is 1 or 2.

In another embodiment $R_1$ is —C(O)$R_5$; n is 0; $R_3$ is —C(O)NH$R_5$, $R_5$ is

p is 1; and $R_6$ is halo and is in the para position.

In another embodiment $R_1$ is —C(O)$R_5$; n is 0; $R_3$ is —C(O)NH$R_5$; $R_5$ is

p is 1; and $R_6$ is halo and is in a meta position.

In another embodiment $R_1$ is —C(O)$R_5$; n is 0; $R_3$ is —C(O)NH$R_5$; $R_5$ is

p is 1; and $R_6$ is halo and is in an ortho position.

In another embodiment $R_1$ is —C(O)$R_5$; n is 0; $R_3$ is —C(O)NH$R_5$; $R_5$ is

p is 2; and each $R_6$ is independently -halo.

In another embodiment $R_1$ is —C(O)$R_5$; n is 0; $R_3$ is —C(O)NH$R_5$; $R_5$ is

p is 2; each $R_6$ is independently -halo; and one $R_6$ is in the para position and the other $R_6$ is in a meta position.

In another embodiment $R_1$ is —C(O)$R_5$; n is 0; $R_3$ is —C(O)NH$R_5$; $R_5$ is

p is 2; each $R_6$ is independently -halo; and one $R_6$ is in the para position and the other $R_6$ is in an ortho position.

In another embodiment $R_1$ is —C(O)$R_5$; n is 0; $R_3$ is —C(O)NH$R_5$; $R_5$ is

p is 2; and one $R_6$ is in an ortho position and the other $R_6$ is in a meta position.

In another embodiment, $R_1$ is —C(O)N$R_5R_5$.

In another embodiment $R_1$ is —C(O)N$R_5R_5$; n is 0; and $R_3$ is -halo.

In another embodiment $R_1$ is —C(O)N$R_5R_5$; n is 0; and $R_3$ is —C(O)$R_5$.

In another embodiment $R_1$ is —C(O)N$R_5R_5$; n is 0; and $R_3$ is —C(O)NHC(O)$R_5$.

In another embodiment $R_1$ is —C(O)N$R_5R_5$; n is 0; and $R_3$ is —H.

In another embodiment $R_1$ is —C(O)N$R_5R_5$; n is 0; and $R_3$ is —CO$_2$(CH$_2$)$_m$($R_5$).

In another embodiment $R_1$ is —C(O)N$R_5R_5$; n is 0; and $R_3$ is —NHC(O)N($R_5$)($R_5$).

In another embodiment $R_1$ is —C(O)N$R_5R_5$; n is 0; and $R_3$ is —C(O)N($R_5$)($R_5$).

In another embodiment $R_1$ is —C(O)N$R_5R_5$; n is 0; and $R_3$ is —C(O)NH$R_5$.

In another embodiment $R_1$ is —C(O)N$R_5R_5$; n is 0; $R_3$ is —C(O)NH$R_5$; and $R_5$ is

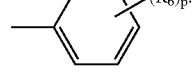

In another embodiment $R_1$ is —C(O)NR$_5$R$_5$; n is 0; $R_3$ is —C(O)NHR$_5$; $R_5$ is

and p is an integer from 1 to 3.

In another embodiment $R_1$ is —C(O)NR$_5$R$_5$; n is 0; $R_3$ is —C(O)NHR$_5$; $R_5$ is

and p is 1 or 2.

In another embodiment $R_1$ is —C(O)NR$_5$R$_5$; n is 0; $R_3$ is —C(O)NHR$_5$; $R_5$ is

p is 1; and $R_6$ is halo and is in the para position.

In another embodiment $R_1$ is —C(O)NR$_5$R$_5$; n is 0; $R_3$ is —C(O)NHR$_5$, $R_5$ is

p is 1; and $R_6$ is halo and is in a meta position.

In another embodiment $R_1$ is —C(O)NR$_5$R$_5$; n is 0; $R_3$ is —C(O)NHR$_5$; $R_5$ is

p is 1; and $R_6$ is halo and is in an ortho position.

In another embodiment $R_1$ is —C(O)NR$_5$R$_5$; n is 0; $R_3$ is —C(O)NR$_5$; $R_5$ is

p is 2; and each $R_6$ is independently -halo.

In another embodiment $R_1$ is —C(O)NR$_5$R$_5$; n is 0; $R_3$ is —C(O)NHR$_5$; $R_5$ is

p is 2; each $R_6$ is independently -halo; and one $R_6$ is in the para position and the other $R_6$ is in a meta position.

In another embodiment $R_1$ is —C(O)NR$_5$R$_5$; n is 0; $R_3$ is —C(O)NHR$_5$, $R_5$ is

p is 2; each $R_6$ is independently -halo; and one $R_6$ is in the para position and the other $R_6$ is in an ortho position.

In another embodiment $R_1$ is —C(O)NR$_5$R$_5$; n is 0; $R_3$ is —C(O)NHR$_5$; $R_5$ is

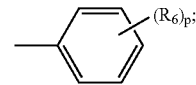

p is 2; and one $R_6$ is in an ortho position and the other $R_6$ is in a meta position.

In another embodiment, the compounds of formula (Ib) are the compounds of formula (Ia), above.

Illustrative compounds of formula (Ib) are compounds and pharmaceutically acceptable salts or hydrates of Formulas AA–EG and compounds having the following structure:

Compound EH

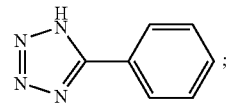

Compound EI

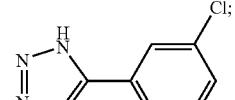

Compound EJ

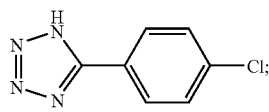

Compound EK

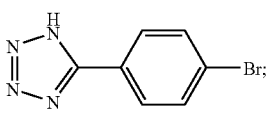

Compound EL

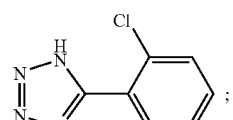

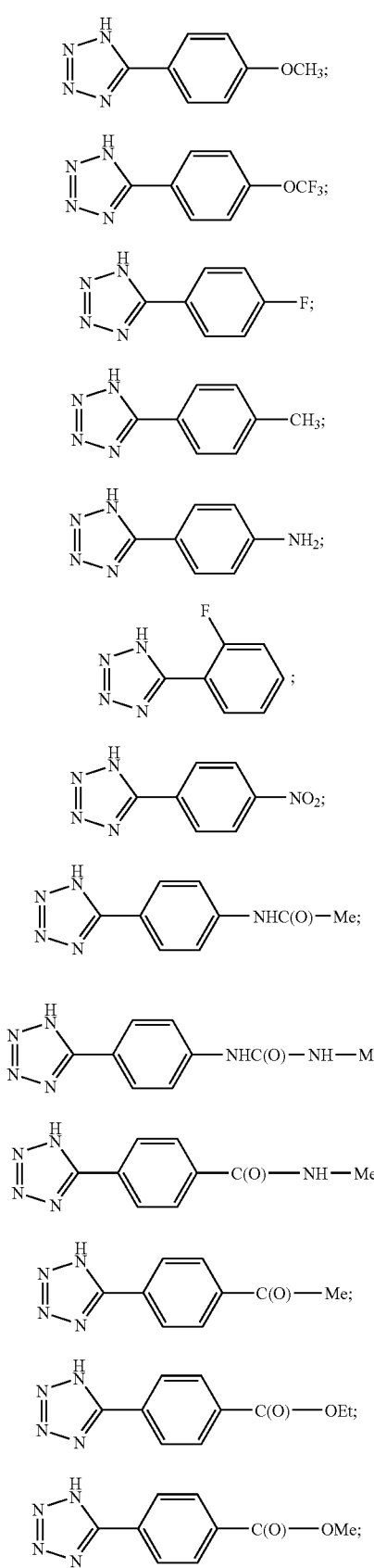
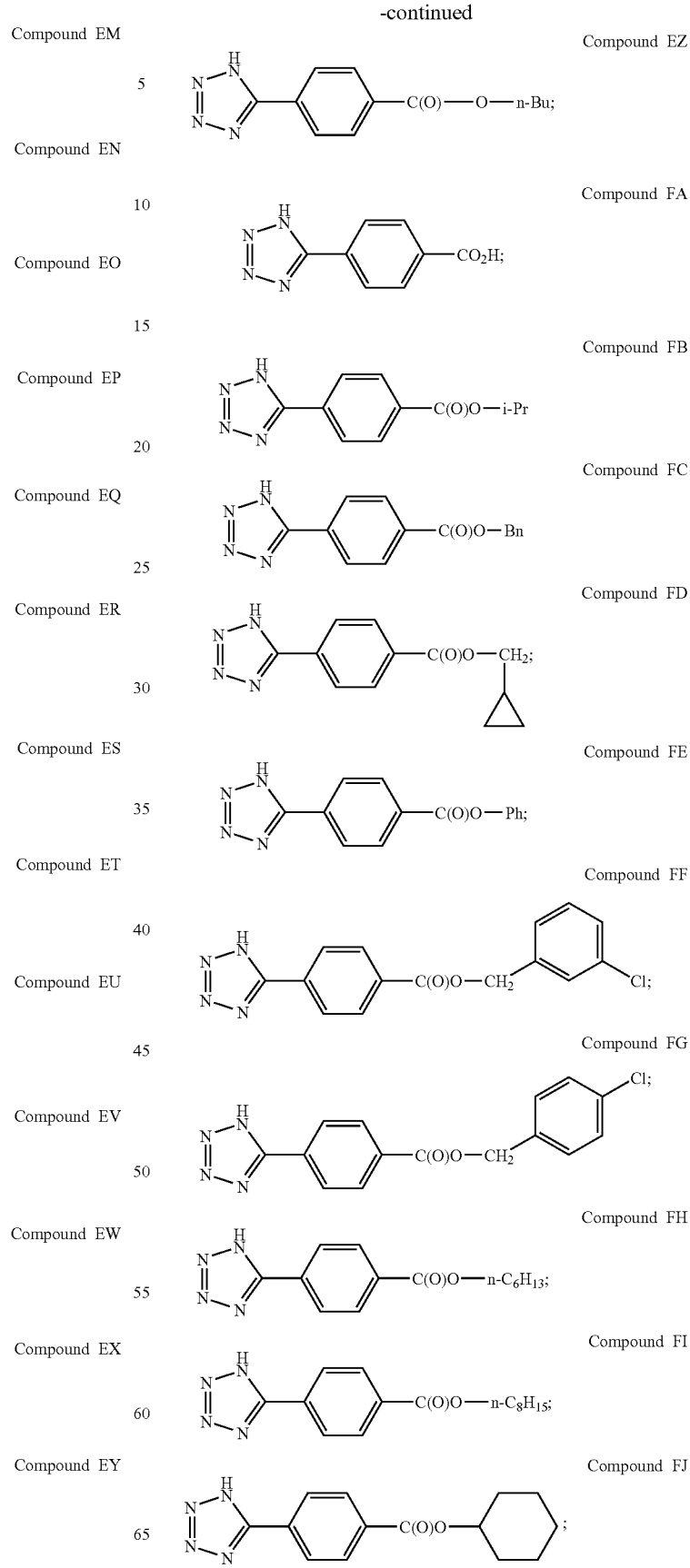

-continued

Compound FK

Compound FL

Compound FM

Compound FN

Compound FO

Compound FP

Compound FQ

Compound FR

Compound FS

Compound FT

-continued

Compound FU

Compound FV

Compound FW

Compound FX

Compound FY

Compound FZ

Compound GA

Compound GB

Compound GC

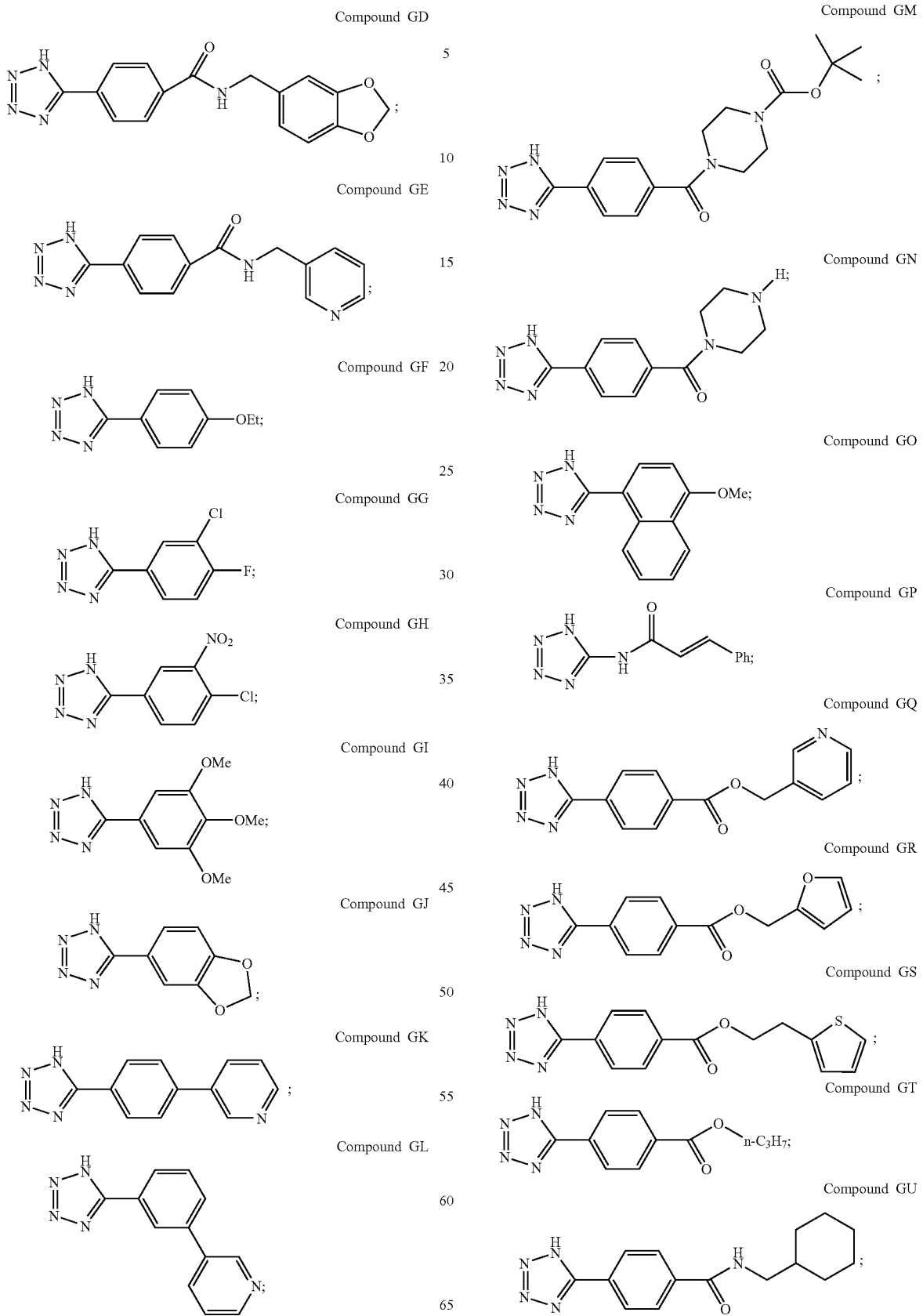

-continued
Compound GV
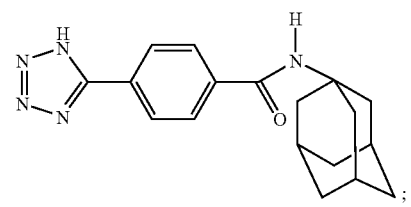
Compound GW
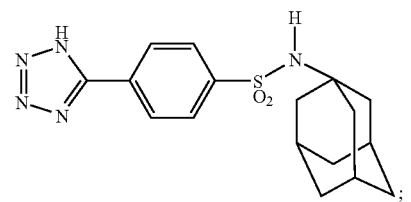
Compound GX
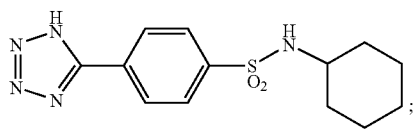
Compound GY
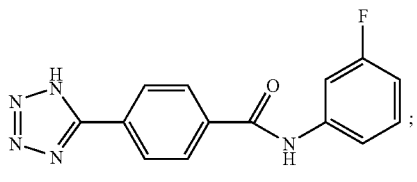
Compound GZ
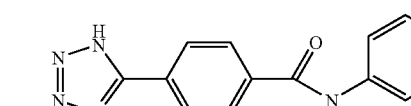
Compound HA
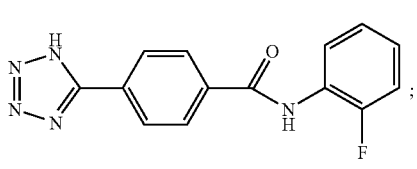
Compound HB
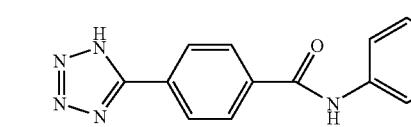
Compound HC
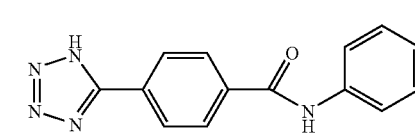
Compound HD
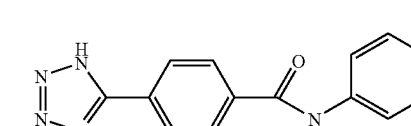
Compound HE
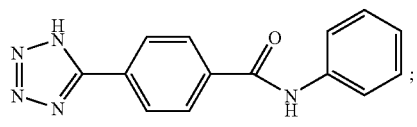
-continued
Compound HF
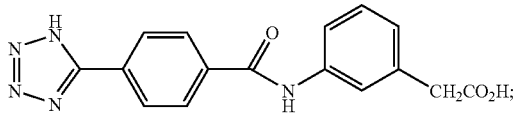
Compound HG
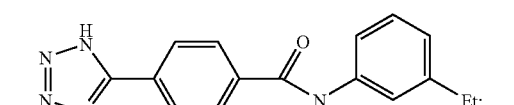
Compound HH
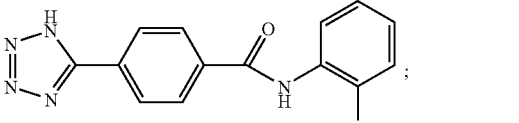
Compound HI
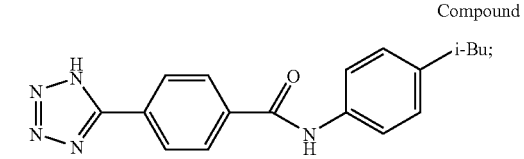
Compound HJ
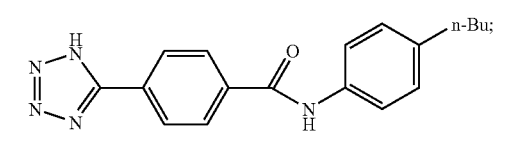
Compound HK
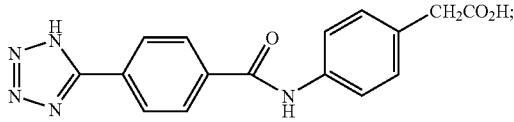
Compound HL
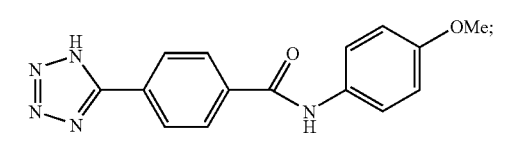
Compound HM
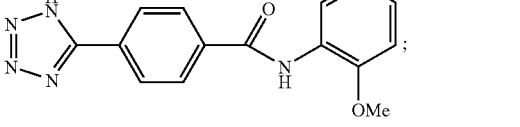
Compound HN
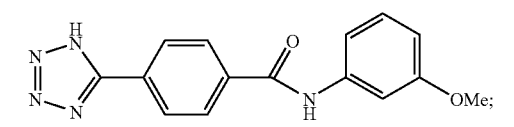
Compound HO
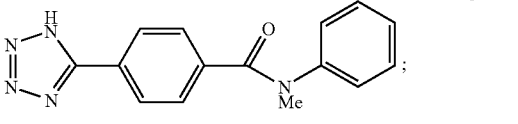

-continued
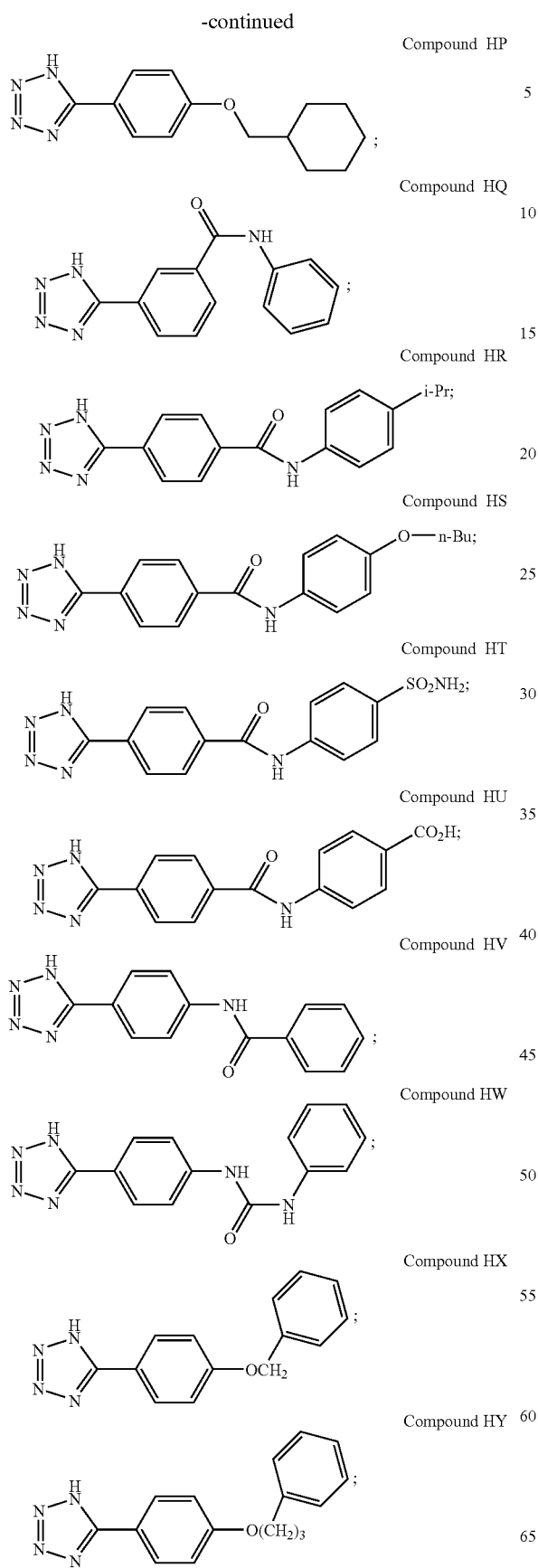
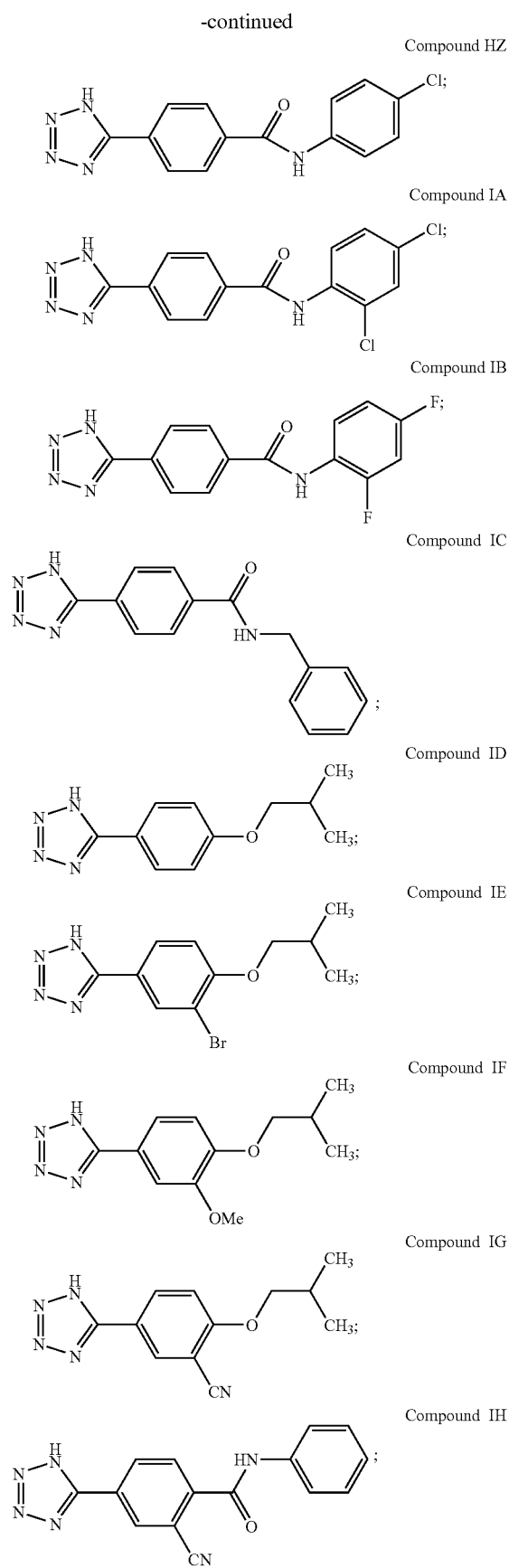

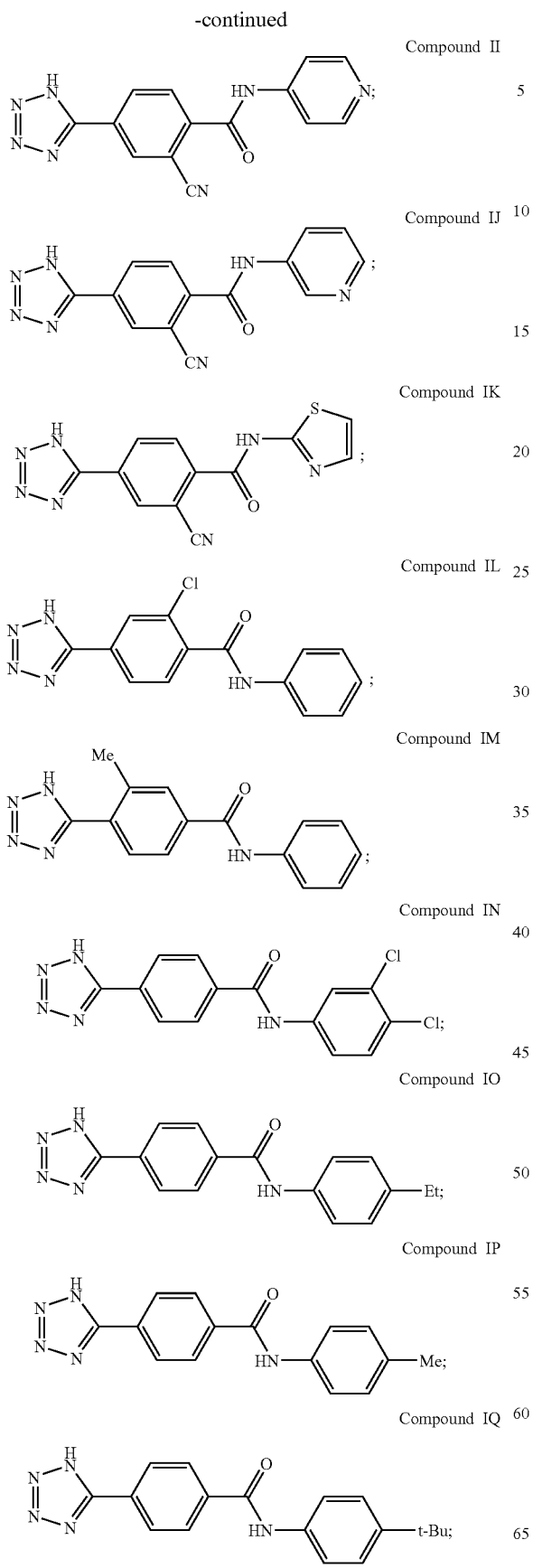

Compound II

Compound IJ

Compound IK

Compound IL

Compound IM

Compound IN

Compound IO

Compound IP

Compound IQ

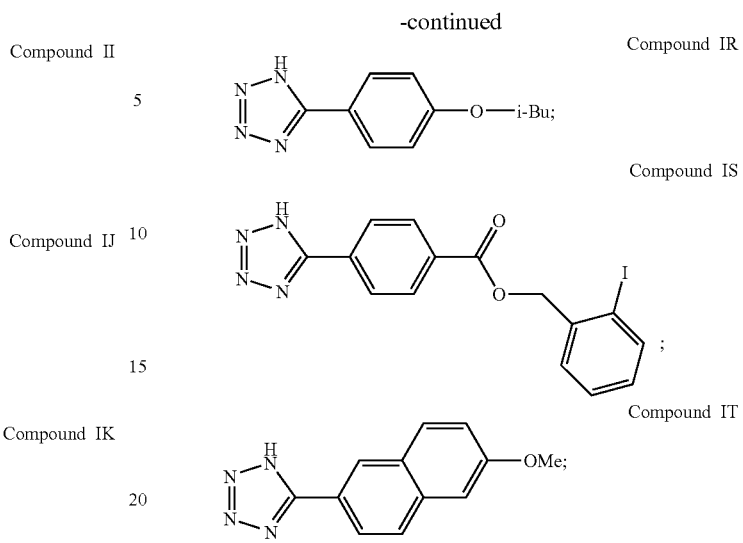

Compound IR

Compound IS

Compound IT and pharmaceutically acceptable salts or hydrates thereof.

4.4. Methods for Making the 5-Aryltetrazole Compounds

The 5-Aryltetrazole Compounds can be made using conventional organic synthesis and/or by the following illustrative methods. General procedures for the synthesis of aryl tetrazoles are provided in, Butler, R. N., *Comprehensive Heterocyclic Chemistry Vol. IV,* 664–668 (1996). Katritzky et al. Eds.

4.4.1. Method A

The 5-Aryltetrazole Compounds of formula (Ib) can be obtained by contacting a compound of formula A with an with an azide (e.g., sodium azide ("NaN$_3$")) at reflux, (e.g., about 100° C.), in the presence of zinc bromide ("ZnBr$_2$") using water as a solvent as shown below in Scheme A. Compounds of formula A can be obtained commercially or made readily by those skilled in the art. A representative procedure for obtaining a 5-Aryltetrazole Compounds of formula (Ib) from a substituted phenyl nitrile in the presence of sodium azide is provided in Sharpless et al., *J. Org. Chem.* 7945–7950 (2001).

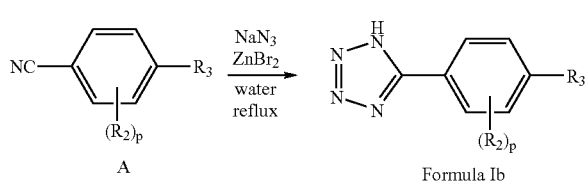

Scheme A

4.4.2. Method B

In another embodiment, a 5-Aryltetrazole Compounds of formula (Ib) can be obtained by contacting a compound of formula A with an azide, (e.g., azidotrimethylsilane ("TMSN$_3$")) and a catalytic amount of dibutyl tin oxide ("n-Bu₂SnO") in refluxing toluene as a solvent as shown below in Scheme B. Methods for obtaining tetrazoles from nitriles and TMSN₃ are provided in, for example, Curran et al., *Tetrahedron,* 1999, 55, 8997–9006.

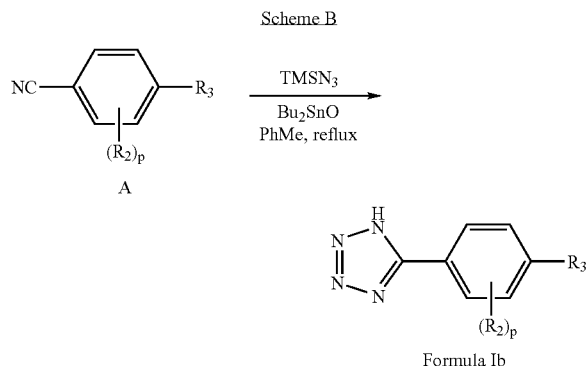

4.4.3. Method C

The 5-Aryltetrazole Compounds of formula (Ib) can be converted to 5-Aryltetrazole compounds of formula (Ia) by contacting the compound of formula (Ib) with an alkyl chlorocarbonate or carbonic acid anhydride under conditions suitable for the formation of a carbamate as shown in Scheme C. Methods for obtaining carbamates from amines and carbonates are provided in, for example, Raucher et al., *Synthetic Commun.* 1985, 15, 1025. For example, illustrative compounds AA–AZ, BA–BZ, CA–CZ, DA–DZ, EA–EG can be made using this method.

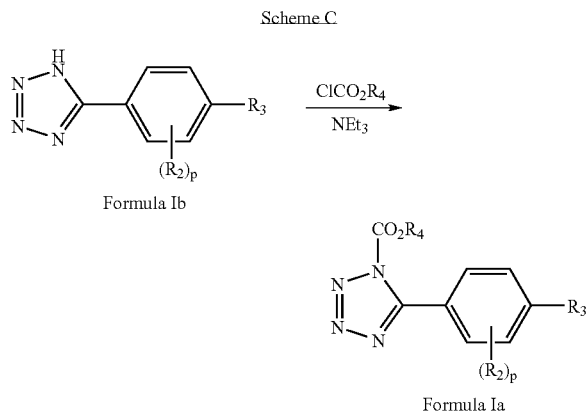

5-Aryltetrazole Compounds can have asymmetric centers and therefore can exist in particular enantiomeric and/or diastereomeric forms. A 5-Aryltetrazole Compound can be in the form of an optical isomer or a diastereomer. Accordingly, the invention encompasses 5-Aryltetrazole Compounds and their uses as described herein in the form of their optical isomers, diastereomers, and mixtures thereof, including a racemic mixture.

In addition, one or more hydrogen, carbon or other atoms of a 5-Aryltetrazole Compound can be replaced by an isotope of the hydrogen, carbon, or other atom. Such compounds, which are encompassed by the present invention, are useful as research and diagnostic tools in metabolism pharmokinetic studies and binding assays.

4.5. Prophylactic and/or Therapeutic Uses of the 5-Aryltetrazole Compounds

In accordance with the invention, an effective amount of a 5-Aryltetrazole Compound, or a pharmaceutical composition comprising a 5-Aryltetrazole Compound is administered to an animal in need of treatment or prevention of an inflammation disease, reperfusion disease, hyperuricemia, gout, tumor-lysis syndrome, or an inflammatory bowel disorder. In one embodiment, an effective amount of a 5-Aryltetrazole Compound can be used to treat or prevent any condition responsive to xanthine-oxidase inhibition. Examples of conditions responsive to xanthine oxidase inhibition include, but are not limited to, inflammation diseases, reperfusion diseases, hyperuricemia, gout, tumor-lysis syndrome, or inflammatory bowel disorders. In another embodiment, an effective amount of a 5-Aryltetrazole Compound can be used to treat or prevent an inflammation disease, a reperfusion disease, hyperuricemia, gout, tumor-lysis syndrome, or an inflammatory bowel disorder.

Examples of inflammation diseases include, but are not limited to, chronic inflammatory disorders of the joints including arthritis, e.g., rheumatoid arthritis and osteoarthritis; respiratory distress syndrome, inflammatory bowel diseases such as ileitis, ulcerative colitis and Crohn's disease; and inflammatory lung disorders such as asthma and chronic obstructive airway disease, inflammatory disorders of the eye such as corneal dystrophy, trachoma, onchocerciasis, uveitis, sympathetic ophthalmitis, and endophthalmitis; inflammatory disorders of the gum, e.g., periodontitis and gingivitis; tuberculosis; leprosy; inflammatory diseases of the kidney including glomerulonephritis and nephrosis; inflammatory disorders of the skin including acne, sclerodermatitis, psoriasis, eczema, photoaging and wrinkles; inflammatory diseases of the central nervous system, including AIDS-related neurodegeneration, stroke, neurotrauma, Alzheimer's disease, encephalomyelitis and viral or autoimmune encephalitis; autoimmune diseases including immune-complex vasculitis, systemic lupus and erythematodes; systemic lupus erythematosus (SLE); and inflammatory diseases of the heart such as cardiomyopathy.

Examples of reperfusion disease include, but are not limited to, shock and sepsis. Shock can be septic shock, e.g., gram positive bacteria-mediated circulatory shock, gram negative bacteria-mediated circulatory shock, hemorrhagic shock, anaphylactic shock, shock associated with systemic inflammation, shock associated with pro-inflammatory cytokines, and shock associated with systemic inflammatory response syndrome (SIRS). The 5-Aryltetrazole Compounds can also be used to prevent or treat circulatory shock, such as shock occurring as a result of gram negative and gram positive sepsis, trauma, hemorrhage, burn injury, anaphylaxis, cytokine immunotherapy, liver failure, kidney failure or systemic inflammatory response syndrome. Other examples of reperfusion disease are disease arising from solid-organ transplantation, cardiopulmonary bypass surgery, compartment syndrome, crush injury, splanchnic ischemia-reperfusion, myocardial infarction and stroke.

Examples of hyperuricemia include, but are not limited to, gout; tumor-lysis syndrome; idiopathic hyperuricemia; hyperuricemia inherited including, but not limited to, hyperuricemia due to PP-ribose-P synthetase overactivity; hypoxanthine-gaunine phosphoribosyltransferase deficiency; glucose-6-phosphate deficiency; Gierke's glycogen storage disease; chronic hemolytic hyperuricemia including, but not limited to, erythroid, myeloid, and lymphoid proliferative hyperuricemia; renal mechanistic hyperuricemia including, but not limited to, familial progressive renal insufficiency, acquired chronic renal insufficiency, drug related renal insufficiency, and endogenous renal production disorders.

Examples of tumor-lysis syndrome include, but are not limited to, tumor-lysis syndrome resulting from chemotherapy treatment in patients with cancer, including but not limited to, leukemias, lymphomas, small cell lung cancer, and breast cancer. In one embodiment, the tumor-lysis syndrome is that which results from chemotherapy, particularly for treating cancer.

Examples of inflammatory bowel disorders include, but are not limited to, ileitis, including, but not limited to, regional ileitis; colitis, including, but not limited to, ulcerative colitis, collagenous/microscopic colitis, and enterocolitis; Crohn's disease; and pouchitis.

4.6. Methods for Administration

Due to their activity, the 5-Aryltetrazole Compounds are advantageously useful in veterinary and human medicine. As described above, the 5-Aryltetrazole Compounds are useful for treating or preventing an inflammation disease, a reperfusion disease, hyperuricemia, gout, tumor-lysis syndrome, and inflammatory bowel disorders in an animal in need thereof.

When administered to an animal, the 5-Aryltetrazole Compounds are preferably administered as a component of a composition that comprises a pharmaceutically acceptable carrier or vehicle. The present compositions, which comprise a 5-Aryltetrazole Compound, are preferably administered orally. The compositions of the invention can also be administered by any other convenient route, for example, by infusion or bolus injection, by absorption through epithelial or mucocutaneous linings (e.g., oral mucosa, rectal, and intestinal mucosa, etc.) and may be administered together with another therapeutic agent. Administration can be systemic or local. Various delivery systems are known, e.g., encapsulation in liposomes, microparticles, microcapsules, capsules, etc., and can be used to administer the 5-Aryltetrazole Compounds.

Methods of administration include, but are not limited to, intradermal, intramuscular, intraperitoneal, intravenous, subcutaneous, intranasal, epidural, oral, sublingual, intracerebral, intravaginal, transdermal, rectally, by inhalation, or topically, particularly to the ears, nose, eyes, or skin. The mode of administration is left to the discretion of the practitioner. In most instances, administration will result in the release of the 5-Aryltetrazole Compounds into the bloodstream.

In specific embodiments, it may be desirable to administer the 5-Aryltetrazole Compounds locally. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce the 5-Aryltetrazole Compounds into the central nervous system by any suitable route, including intraventricular, intrathecal, and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the 5-Aryltetrazole Compounds can be formulated as a suppository, with traditional binders and excipients such as triglycerides.

In another embodiment, the 5-Aryltetrazole Compounds can be delivered in a vesicle, in particular a liposome (see Langer, *Science* 249:1527–1533 (1990) and Treat et al., *Liposomes in the Therapy of Infectious Disease and Cancer* 317–327 and 353–365 (1989).

In yet another embodiment, the 5-Aryltetrazole Compounds can be delivered in a controlled-release system (see, e.g., Goodson, in Medical Applications of Controlled Release, supra, vol. 2, pp. 115–138 (1984)). Other controlled-release systems discussed in the review by Langer, *Science* 249:1527–1533 (1990) may be used. In one embodiment, a pump may be used (Langer, *Science* 249:1527–1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled-release system can be placed in proximity of a target of the 5-Aryltetrazole Compound, e.g., the spinal column or brain, thus requiring only a fraction of the systemic dose.

The present compositions can optionally comprise a suitable amount of a pharmaceutically acceptable carrier or vehicle so as to provide the form for proper administration to the animal.

Such pharmaceutical carriers or vehicles can be liquids, such as water and oils, including those of petroleum, animal, vegetable, or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating, and coloring agents may be used. When administered to an animal, the pharmaceutically acceptable carriers or vehicles are preferably sterile. Water is a particularly useful vehicle when the 5-Aryltetrazole Compound of the invention is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see e.g., U.S. Pat. No. 5,698,155). Other examples of suitable pharmaceutical excipients are described in *Remington's Pharmaceu-* tical Sciences 1447–1676 (Alfonso R. Gennaro ed., 19th ed. 1995), incorporated herein by reference.

In one embodiment, the 5-Aryltetrazole Compounds are formulated in accordance with routine procedures as a composition adapted for oral administration to human beings. Compositions for oral delivery may be in the form of tablets, lozenges, aqueous or oily suspensions, granules, powders, emulsions, capsules, syrups, or elixirs, for example. Orally administered compositions may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard excipients such as mannitol, lactose, starch, magnesium stearate, sodium saccharin, cellulose and magnesium carbonate. Such excipients are preferably of pharmaceutical grade.

In another embodiment, the 5-Aryltetrazole Compounds can be formulated for intravenous administration. Typically, compositions for intravenous administration comprise sterile isotonic aqueous buffer. Where necessary, the compositions may also include a solubilizing agent. Compositions for intravenous administration may optionally include a local anesthetic such as lignocaine to lessen pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the 5-Aryltetrazole Compounds are to be administered by infusion, they can be dispensed, for example, with an infusion bottle containing sterile pharmaceutical grade water or saline. Where the 5-Aryltetrazole Compounds are administered by injection, an ampoule of sterile water for injection or saline can be provided so that the ingredients may be mixed prior to administration.

The 5-Aryltetrazole Compounds of the invention can be administered by controlled-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

The amount of the 5-Aryltetrazole Compound that is effective in the treatment or prevention of an inflammation disease, a reperfusion disease, tumor-lysis syndrome, hyperuricemia, gout, or an inflammatory bowel disorder will depend on the nature of the disorder or condition causing the inflammation disease, reperfusion disease, hyperuricemia, gout, tumor-lysis syndrome, or an inflammatory bowel disorder and can be determined by standard clinical techniques. In addition, in vitro or in vivo assays may optionally be employed to help identify optimal dosage ranges. The precise dose to be employed will also depend on the route of administration, and the seriousness of the inflammation disease, a reperfusion disease, hyperuricemia, gout, gout, tumor-lysis syndrome, or an inflammatory bowel disorder and should be decided according to the judgment of the practitioner and each patient's circumstances in view of published clinical studies. Administration can be at a dose from about 0.1 to about 500 mg/kg/day of the 5-Aryltetrazole Compound to animal in need thereof. Suitable dosages, however, range from about 0.1 milligrams to about 500 milligrams about every 4 h, although typically about 100 mg or less. Preferably the dosage ranges from about 0.01 milligrams to about 500 milligrams of a 5-Aryltetrazole Compound about every 4 h, more preferably about 0.020 milligrams to about 50 milligrams about every 4 h, and most preferably about 0.025 milligrams to about 20 milligrams about every 4 h. The dosage amounts described herein refer to total amounts administered; that is, if more than one 5-Aryltetrazole Compound is administered, the preferred dosages correspond to the total amount administered.

The 5-Aryltetrazole Compounds are preferably assayed in vitro or in vivo, for the desired therapeutic or prophylactic activity, prior to use in humans. Animal model systems can be used to demonstrate safety and efficacy.

The present methods for treating or preventing inflammation disease, a reperfusion disease, hyperuricemia, gout, tumor-lysis syndrome, or an inflammatory bowel disorder in an animal in need thereof can further comprise administering to the animal being administered a 5-Aryltetrazole Compound an effective amount of one or more other therapeutic agents.

The other therapeutic agent includes, but is not limited to, a non-steroid antiinflammatory agent, an antidepressant, and mixtures thereof.

Effective amounts of the other therapeutic agents are well known to those skilled in the art. However, it is well within the skilled artisan's purview to determine the other therapeutic agent's optimal effective-amount range. In one embodiment of the invention where another therapeutic agent is administered to an animal, the effective amount of the 5-Aryltetrazole Compound is less than its effective amount would be where the other therapeutic agent is not administered. In another embodiment, the 5-Aryltetrazole Compound and the other therapeutic agent act synergistically to treat inflammation disease, reperfusion disease, hyperuricemia, gout, tumor-lysis syndrome, or an inflammatory bowel disorder.

The other therapeutic agent can be a non-steroidal anti-inflammatory agent. Useful non-steroidal anti-inflammatory agents, include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone and pharmaceutically acceptable salts thereof and mixtures thereof. For a more detailed description of the NSAIDs, see Paul A. Insel, *Analgesic-Antipyretic and Antiinflammatory Agents and Drugs Employed in the Treatment of Gout*, in Goodman & Gilman's The Pharmacological Basis of Therapeutics 617–57 (Perry B. Molinhoff and Raymond W. Ruddon eds., $9^{th \ ed}$ 1996) and Glen R. Hanson, *Analgesic, Antipyretic and Anti-Inflammatory Drugs* in Remington: The Science and Practice of Pharmacy Vol II 1196–1221 (A. R. Gennaro ed. 19th ed. 1995) which are hereby incorporated by reference in their entireties.

The other therapeutic agent can be an anticonvulsant. Useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

The other therapeutic agent can be an anti-depressant. Useful antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

The other therapeutic agent can be an anti-hyperuricemic agent. Useful anti-hyperuricemic agents also include, but are not limited to, allopurinol.

The other therapeutic agent can be an agent useful in treating or preventing tumor-lysis syndrome. Therapeutic agents useful for treating or preventing tumor-lysis syndrome also include, but are not limited to, Lasix or Zyloprim.

The other therapeutic agent can be an agent useful in treating or preventing an inflammatory bowel disorder. Therapeutic agents useful for treating or preventing an inflammatory bowel disorder include, but are not limited to, sulfasalazine, olsalazine, and mesalamine.

A 5-Aryltetrazole Compound and the other therapeutic agent can act additively or, more preferably, synergistically. In one embodiment, a 5-Aryltetrazole Compound is administered concurrently with another therapeutic agent. In one embodiment, a composition comprising an effective amount of a 5-Aryltetrazole Compound and an effective amount of another therapeutic agent can be administered. Alternatively, a composition comprising an effective amount of a 5-Aryltetrazole Compound and a different composition comprising an effective amount of another therapeutic agent can be concurrently administered. In another embodiment, an effective amount of a 5-Aryltetrazole Compound is administered prior or subsequent to administration of an effective amount of another therapeutic agent.

4.8. Kits

The invention encompasses kits that can simplify the administration of a 5-Aryltetrazole Compound to an animal.

A typical kit of the invention comprises a unit dosage form of a 5-Aryltetrazole Compound. In one embodiment, the unit dosage form is a container, preferably a sterile container, containing an effective amount of a 5-Aryltetrazole Compound and a pharmaceutically acceptable carrier or excipient. The kit can further comprise a label or printed instructions instructing the use of the 5-Aryltetrazole Compound to treat inflammation disease, reperfusion disease, hyperuricemia, gout, tumor-lysis syndrome, or an inflammatory bowel disorder. The kit can also further comprise a unit dosage form of another therapeutic agent, for example, a container containing an effective amount of the other therapeutic agent. In one embodiment, the kit comprises a container containing an effective amount of a 5-Aryltetrazole Compound and an effective amount of another therapeutic agent. Examples of other therapeutic agents include, but are not limited to, those listed above.

Kits of the invention can further comprise devices that are useful for administering the unit dosage forms. Examples of such devices include, but are not limited to, syringes, drip bags, patches, and inhalers.

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

5. EXAMPLES

5.1. Example 1

Synthesis of Compound HE

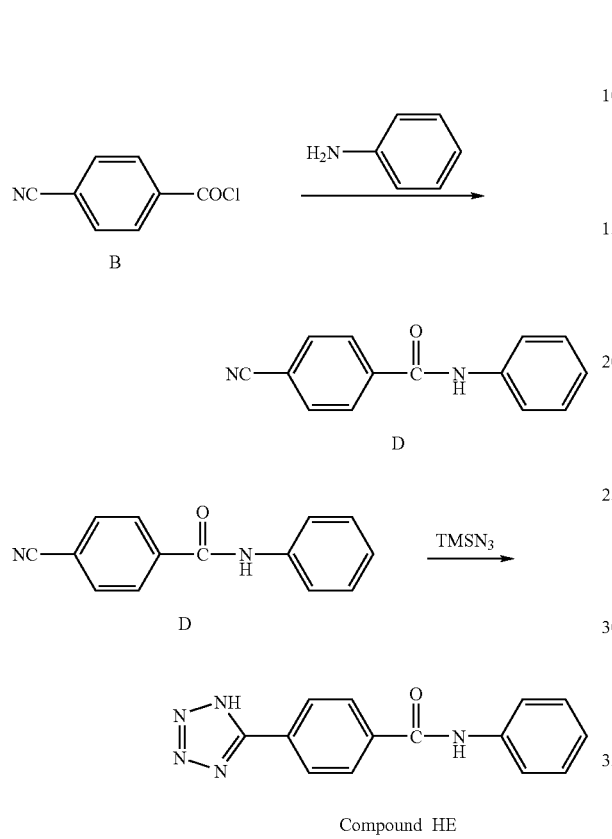

5.2. Example 2

Alternative Synthesis of Compound HE

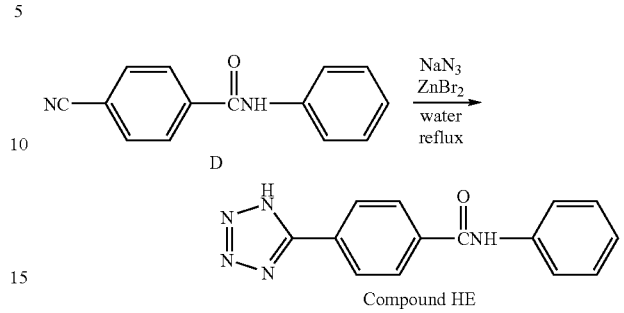

A solution of 4-cyanobenzoylchloride B (0.82 g, 5 mmol) (commercially available from Sigma-Aldrich Co. was stirred in dry toluene (20 mL). Aniline (0.5 mL, 0.55 mmol) was added dropwise, and following the initial exothermic reaction, the suspension was refluxed for 2 h. After cooling to room temperature, hexane (100 mL) was added to the reaction mixture and the precipitate was filtered and washed with hexane to afford Compound D: Yield 2.0 g (90%), $^1$H NMR (DMSO-$d_6$): δ 7.1 (t, 1H, p-H- NHPh) 7.35 (t, 2H, m-H, NHPh), 7.75 (d, 2H, o-H, NHPh); 8.15 (AA'BB', A=27 Hz, 4H, C(O)Ar), 10.45 (s, 1H, C(O)NH).

A mixture of Compound D (2.2 g, 10 mmol), azidotrimethylsilane (2 mL, 15 mmol) and dibutyltin oxide (0.5 g, 2 mmol) in anhydrous toluene (40 mL) was heated at 100° C. for 5 h. The progress of the reaction was monitored by Thin-Layer Chromatography. After completion of the reaction the organic phase was extracted with 1 M NaOH (20 mL). The aqueous layer was washed with ethyl acetate (2×20 mL) and acidified to pH 2 using 2 M HCl. The separated white solid was collected by filtration to provide Compound HE: Yield 1.95 g (75%). $^1$H NMR (DMSO-$d_6$): δ 7.1 (t, 1H, p-H, NHPh) 7.35 (t, 2H, m-H, NHPh), 7.8 (d, 2H, o-H, NHPh); 8.15 (AA'BB', A=12 Hz, 4H, C(O)Ar), 10.4 (s, 1H, C(O)NH). ES/MS: m/z$^+$263 (M$^+$+1, 100%).

A mixture of Compound D (2.2 g, 10 mmol), sodium azide (1.3 g, 20 mmol), zinc bromide (1.15 g, 10 mmol) and isopropanol (5 mL) in water (20 mL) was stirred at reflux for 48 h. After the mixture was cooled to 60° C., 50 mL of 2 M NaOH was added and the suspension was stirred for additional 30 min at this temperature. The precipitate was filtered and the aqueous solution was extracted with ethyl acetate (2×50 mL). The aqueous layer was separated and acidified to pH 2 using 2 M HCl. The precipitate was filtered and washed thoroughly with water to provide Compound HE. Yield 1.3 g (50%).

Experimental data for illustrative 5-Aryltetrazoles Compounds prepared using the methods analogous to those above are given below.

5.3. Example 3

Compounds EV, GC, GD, GE, GM, GN, GU, GV, GY, GZ, HA–HH, HJ–HO, HQ, HU, HZ, IA, IB, IC, II, IJ, IK, IM, IN, IO, and IP Compounds EV, GC, GD, GE, GM, GN, GU, GV, GY, GZ, HA–HH, HJ–HO, HQ, HU, HZ, IA, IB, IC, II, IJ, IK, IM, IN, IO, and IP were prepared according to the method of example 1 using the corresponding amine in place of aniline. Compounds IQ, HR, and HI were prepared according to the method of examples 1 and 2 using the corresponding amine in place of aniline.

Experimental data for illustrative 5-Aryltetrazoles Compounds prepared using the method in Section 5.1 are given below.

5.3.1. Compound GZ $^1$H NMR (DMSO-$D_6$): δ 7.2 (t, 2H, m-H, NHAr), 7.8 (q, 2H, o-H, NHAr), 8.05 (AA'BB', Δ=10 Hz, 4H, C(O)Ar), 10.4 (s, 1H, C(O)NH).

5.3.2. Compound HC $^1$H NMR (DMSO-$D_6$): δ 2.6 (S, 3H, CH$_3$), 7.5 (d, 1H 3-H, NHAr), 7.7 (d, 1H, 4-H, NHAr), 8.1 (m, 5H, 2-H NAr+C(O)Ar), 8.4 (s, 1H, 6-H, NHAr), 10.6 (s, 1H, C(O)NH).

5.3.3. Compound HR $^1$H NMR (DMSO-$D_6$): δ 1.2 (d, 6H, 2CH$_3$), 2.8 (m, 1H, CH(CH$_3$)$_2$), 7.4 (AA'BB', Δ=140 Hz, 4H, C(O)Ar), 8.05 (AA'BB', m, 4H, C(O)Ar), 10.6 (s, 1H, C(O)NH).

5.3.4. Compound HU $^1$H NMR (DMSO-D$_6$): δ 6 7.9 (s, 4H, NHAr), 8.1 (AA'BB', Δ=34 Hz, 4H, C(O)Ar), 10.6 (s, 1H, C(O)NH).

5.3.5. Compound IP $^1$H NMR (DMSO-D$_6$): δ 2.2 (s, 3H, CH$_3$), 7.4 (AA'BB', Δ=154 Hz, 4H, NHAr), 8.05 (AA'BB', Δ=14 Hz, 4H, C(O)Ar), 10.3 (s, 1H, C(O)NH).

5.4. Example 4

Synthesis of Compounds EX–EZ, FB–FZ, GA, GB, GQ–GT, and IS

Compounds EX–EZ, FB–FZ, GA, GB, GQ–GT, and IS were prepared according to Method B (described in Section 4.4 above) from the corresponding esters of 4-cyanobenzoic acid. These esters were obtained from 4-cyanobenzoyl chloride and an alcohol or a halide as described in *Vogel's Textbook of Practical Organic Chemistry* 5th Ed., p. 695. Such alcohols and halides are commercially available.

5.5. Example 5

Synthesis of Compounds IR, HP, HX, HY, ID, IE, IF, AND IG

To a solution of 4-cyanophenol (1.2 g, 10 mmol) in dry DMF (20 mL) was added triethylamine (20 mmol) followed by i-butyl bromide (2.7 g, 20 mmol). The resulting reaction mixture was stirred at 100° C. for 6 h. After cooling to room temperature, the reaction mixture was diluted with water (100 mL) and extracted with ethyl acetate (2×40 mL). The organic layer was washed with 4 M KOH (3×30 mL) and then with water, dried over Na$_2$SO$_4$ and concentrated under vacuum to provide 1.5 g (85%) 4-iso-butoxybenzonitrile that was used for the next step without further purification. $^1$H NMR (DMSO-D$_6$): δ 0.95 (d, 6H, 2CH$_3$), 2.0 (m, 1H, CH(CH$_3$)$_2$), 3.8 (d, 2H, CH$_2$), 7.4 (AA'BB', Δ=270 Hz, 4H, Ar).

A mixture of 4-iso-butoxybenzonitrile (1.75 g, 10 mmol), azidotrimethyl-silane (2 mL, 15 mmol) and dibutyltinoxide (0.5 g, 2 mmol) in anhydrous toluene (40 mL) was heated at 100° C. for 18 h. While still hot, the organic phase was extracted with 20 mL 1 M NaOH, aqueous layer was washed with ethyl acetate (2×20 mL) and acidified to pH 2 using 2 M HCl. The resulting white solid was collected by filtration to provide Compound IR: Yield 1.2 g (55%). $^1$H NMR (DMSO-d$_6$): δ 0.95 (d, 6H, 2CH$_3$), 2.0 (m, 1H, CH(CH$_3$)$_2$), 3.8 (d, 2H, CH$_2$), 7.5 (AA'BB', Δ=295 Hz, 4H, Ar).

Compounds HP, HX, HY, ID, IE, and IF were prepared analogously starting from the commercially available substituted 4-cyanophenols. 3-Bromocyanophenol used in the synthesis of the compound IE was prepared by bromination of 4-cyanophenol in acetic acid using bromine as described in Minoshima et. al., JP 10139770 (1998). Compound IG was prepared be reacting Compound IE with potassium cyanide in the presence of catalytic amount of Ni[(PPh$_3$)$_4$] in N-methylpyrrolidone as described in Minoshima et. al., JP 10139770 (1998).

5.6. Example 6

Compounds of Formula EH–ES, EW, FA, GG, GH, GI–GL, GO, and IT

These compounds were obtained from the commercially available substituted benzonitriles using the Method B.

5.7. Example 7

Compounds of Formula DL

Compounds of the formula DL (R$_4$=Bzl, Et, tert-Bu) were obtained from compound HE using Method C (described in Section 4.4), using commercially available CbzCl, ClCO$_2$Et, and Boc$_2$O, respectively.

5.8. Example 8

Compound ET

Compound ET was synthesized by reacting a commercially available 4-aminobenzonitrile with acetic anhydride as described in *Vogel's Textbook of Practical Organic Chemistry* 5th Ed., p. 917 and then converting a resulting 4-acetylaminobenzonitrile to compound ET following the Method B.

5.9. Example 9

Compounds of Formula EU and HW

Compounds EU and HW were synthesized by reacting 4-aminobenzonitrile with methylisocyanate or phenylisocyanate, respectively, as described in Vishnyakova et al., *Russ. Chem. Rev.*, 1985, 54, 249 and then converting the resulting urea derivative to the tetrazole compound following Method B.

5.10. Example 10

Compound GP

Compound GP was prepared by reacting commercially available 5-aminotetrazole with cinnamoyl chloride as described in *Vogel's Textbook of Practical Organic Chemistry* 5th Ed., p. 917.

5.11. Example 11

Compounds of Formula GW and GX

Compounds GW and GX were prepared by reacting a commercially available 4-cyanobenzoylsulfonyl chloride with amine and then converting a resulting amide to tetrazole as described in Example 5.1. above.

5.12. Example 12

Compound HV

Compound HV was prepared by benzoylation of 4-aminobenzonitrile as described in Vogel's Textbook of Practical Organic Chemistry 5th Ed., p. 917 and then converting a resulting N-benzoyl-4-cyanoaniline to compound HV following the Method B (Sect. 4.4).

5.13. Example 13

Xanthine Oxidase Inhibitory Activity of Illustrative 5-Aryl Tetrazole Compounds A typical assay for the detection of xanthine oxidase inhibitory activity of the 5-Aryltetrazole Compounds involved use of a 96 well plate setup. Analysis of the sample utilized a Spectrophotometer with a SoftMax Pro Program set at a kinetic reading at a wavelength of 295 nm with a runtime of 10 minutes taking a reading at 12 second intervals. Before the first reading the sample was mixed using an automixer for five seconds and between readings the sample was mixed for three seconds.

Sample Preparation: Approximately 1–2 mg of the 5-Aryltetrazole Compound to be analyzed was placed in a 5 mL vial and dissolved in about 1 mL of DMSO resulting in a 2.5 mM solution.

Well Plate Preparation: Four to eight wells were used for each sample of the 5-Aryltetrazole Compound tested. In each well was added 200 μL of Phosphate-buffered saline (50 mM), 20 μL of xanthine (0.5 mg/mL in water), 10 μL of the 2.5 mM solution of sample (prepared as described above), and 20 μL of xanthine oxidase (1/100×40 mL PBS). The xanthine oxidase was kept on ice and was added immediately before the plate was run on the spectrophotometer. A control well was also prepared using only DMSO.

The following table shows concentrations of illustrative 5-Aryltetrazole Compounds providing xanthine-oxidase inhibition. Without being limited by theory, compounds that inhibit xanthine oxidase are useful for treating or preventing an inflammation disease, a reperfusion disease, hyperuricemia, gout, tumor-lysis syndrome, or an inflammatory bowel disorder.

PERCENT XANTHINE OXIDASE INHIBITION

| Compound | 100 | 10 | 1 | 0.1 | 0.05 | 0.03 | 0.01 |
| --- | --- | --- | --- | --- | --- | --- | --- |
| | | | | Concentration (μM) | | | |
| EH | 10 | NT | NT | NT | NT | NT | NT |
| EI | 34 | NT | NT | NT | NT | NT | NT |
| EJ | 69 | 27 | NT | NT | NT | NT | NT |
| EL | 7 | 5 | NT | NT | NT | NT | NT |
| EK | 67 | 21 | NT | NT | NT | NT | NT |
| EM | 71 | 30 | NT | NT | NT | NT | NT |
| EN | 55 | 14 | NT | NT | NT | NT | NT |
| EO | 78 | 19 | NT | NT | NT | NT | NT |
| EP | 32 | 3 | NT | NT | NT | NT | NT |
| ER | 21 | 3 | NT | NT | NT | NT | NT |
| EQ | 30 | 3 | NT | NT | NT | NT | NT |
| ES | 99 | 81 | 34 | NT | NT | NT | NT |
| ET | 40 | NT | NT | NT | NT | NT | NT |
| EU | 10 | NT | NT | NT | NT | NT | NT |
| EV | 67 | 70 | 15 | NT | NT | NT | NT |
| EW | 92 | 54 | 9 | NT | NT | NT | NT |
| EX | 100 | 92 | 64 | NT | NT | NT | NT |
| EY | 100 | 82 | 39 | NT | NT | NT | NT |
| EZ | 95 | 95 | 73 | NT | NT | NT | NT |
| FA | 91 | 56 | 11 | NT | NT | NT | NT |
| FB | 100 | 97 | 88 | NT | NT | NT | NT |
| FC | 100 | 100 | 78 | NT | NT | NT | NT |
| FD | 100 | 97 | 82 | NT | NT | NT | NT |
| FE | NT | NT | 100 | 97 | 52 | NT | NT |
| FF | 100 | 82 | 79 | NT | NT | NT | NT |
| FG | NT | NT | 100 | 100 | 59 | NT | NT |
| FH | 97 | 79 | 28 | NT | NT | NT | NT |
| FI | 89 | 97 | 90 | NT | NT | NT | NT |
| FJ | NT | NT | 100 | 91 | NT | 65 | NT |
| FK | NT | NT | 100 | 95 | NT | 75 | NT |
| FL | NT | NT | 99 | 59 | NT | NT | 12 |
| IS | NT | NT | 100 | 89 | NT | NT | 18 |
| FM | NT | NT | 46 | 12 | NT | NT | 3 |
| FN | NT | NT | 4 | NT | NT | NT | NT |
| FO | NT | NT | 76 | 28 | NT | NT | 8 |
| FP | NT | NT | 9 | NT | NT | NT | NT |
| FQ | NT | NT | 82 | 18 | NT | NT | 6 |
| FR | NT | NT | 92 | 65 | NT | NT | 9 |
| FS | NT | NT | 78 | 35 | NT | NT | 0 |
| FT | NT | NT | 48 | 8 | NT | NT | 0 |
| FU | NT | NT | 95 | 68 | NT | NT | 13 |
| FV | NT | NT | 94 | 53 | NT | NT | 8 |
| FW | NT | NT | 94 | 69 | NT | NT | 17 |
| FX | NT | NT | 95 | 73 | NT | NT | 14 |
| FY | NT | NT | 39 | 9 | NT | NT | 5 |
| FZ | NT | NT | 100 | 84 | NT | NT | 19 |
| GA | NT | NT | 76 | 11 | NT | NT | 19 |
| GB | NT | NT | 8 | NT | NT | NT | NT |
| GC | NT | NT | 61 | 10 | NT | NT | NT |
| GD | NT | NT | 25 | NT | NT | NT | NT |
| GE | NT | NT | 25 | NT | NT | NT | NT |
| GF | 60 | NT | NT | NT | NT | NT | NT |
| GG | 33 | NT | NT | NT | NT | NT | NT |
| GH | 80 | NT | NT | NT | NT | NT | NT |
| GI | 22 | NT | NT | NT | NT | NT | NT |
| GJ | 48 | NT | NT | NT | NT | NT | NT |
| GK | 70 | 24 | 14 | NT | NT | NT | NT |
| GL | 2 | NT | NT | NT | NT | NT | NT |
| GM | 43 | NT | NT | NT | NT | NT | NT |
| GN | 0 | NT | NT | NT | NT | NT | NT |
| IT | 85 | 56 | 14 | NT | NT | NT | NT |
| GO | 27 | NT | NT | NT | NT | NT | NT |
| GP | 42 | 13 | 10 | NT | NT | NT | NT |
| GQ | NT | NT | 98 | 95 | 46 | NT | NT |
| GR | NT | NT | 100 | 91 | 41 | NT | NT |
| GS | NT | NT | 95 | 97 | 53 | NT | NT |
| GT | NT | NT | 95 | 95 | 34 | NT | NT |
| GU | NT | NT | 55 | 16 | NT | 8 | NT |
| GV | NT | NT | 62 | 23 | NT | 15 | NT |
| GW | NT | NT | 0 | NT | NT | NT | NT |
| GX | NT | NT | 0 | NT | NT | NT | NT |
| GY | NT | NT | 89 | 62 | NT | 32 | NT |
| GZ | NT | NT | 92 | 59 | NT | 37 | NT |
| HA | NT | NT | 86 | 45 | NT | 20 | NT |
| HB | NT | NT | 88 | 41 | NT | 20 | NT |
| HC | NT | NT | 90 | 54 | NT | 31 | NT |
| HD | NT | NT | 94 | 64 | NT | 38 | NT |
| HE | NT | NT | 100 | 81 | NT | 60 | NT |
| HF | NT | NT | 72 | 37 | NT | 13 | NT |
| HG | NT | NT | 87 | 38 | NT | 22 | NT |
| HH | NT | NT | 16 | NT | NT | NT | NT |
| HI | NT | NT | 93 | 59 | NT | 33 | NT |
| HJ | NT | NT | 95 | 63 | NT | 33 | NT |
| HK | NT | NT | 90 | 45 | NT | 20 | NT |
| HL | NT | NT | 93 | 58 | NT | 27 | NT |
| HM | NT | NT | 55 | 17 | NT | 9 | NT |
| HN | NT | NT | 86 | 46 | NT | 21 | NT |
| HO | NT | NT | 0 | NT | NT | NT | NT |
| HP | NT | NT | 68 | 21 | NT | NT | NT |
| HQ | NT | NT | 0 | NT | NT | NT | NT |
| HR | NT | NT | 92 | 52 | NT | 28 | NT |
| HS | NT | NT | 64 | 33 | NT | 36 | NT |
| HT | NT | NT | 88 | 47 | NT | 28 | NT |
| HU | NT | NT | 97 | 68 | NT | 44 | NT |
| HV | NT | NT | 56 | 15 | NT | 7 | NT |
| HW | NT | NT | 42 | 9 | NT | 3 | NT |
| HX | NT | NT | 35 | 10 | NT | NT | NT |
| HY | NT | NT | 22 | 9 | NT | NT | NT |
| HZ | NT | NT | 98 | 74 | NT | 46 | NT |
| IA | NT | NT | 86 | 47 | NT | 26 | NT |
| IB | NT | NT | 89 | 52 | NT | 23 | NT |
| IC | NT | NT | NT | 0 | NT | NT | NT |
| ID | NT | NT | 32 | 15 | NT | NT | NT |

-continued

PERCENT XANTHINE OXIDASE INHIBITION

| | Concentration (μM) | | | | | |
|---|---|---|---|---|---|---|
| Compound | 100 | 10 | 1 | 0.1 | 0.05 | 0.03 | 0.01 |
| IE | NT | NT | 31 | 6 | NT | NT | NT |
| IF | NT | NT | 28 | 0 | NT | NT | NT |
| IG | NT | NT | 82 | 32 | NT | 12 | NT |
| IH | NT | NT | 34 | 6 | NT | NT | NT |
| II | NT | NT | 93 | 61 | NT | 33 | NT |
| IJ | NT | NT | 86 | 41 | NT | 23 | NT |
| IK | NT | NT | 79 | 30 | NT | 19 | NT |
| IL | NT | NT | 0 | NT | NT | NT | NT |
| IM | NT | NT | 0 | NT | NT | NT | NT |
| IN | NT | NT | 95 | 68 | NT | 34 | NT |
| IO | NT | NT | 89 | 38 | NT | 16 | NT |
| IP | NT | NT | 88 | 41 | NT | 20 | NT |
| IQ | NT | NT | 83 | 36 | NT | 18 | NT |
| IR | NT | NT | 98 | 74 | NT | 46 | NT |

The term "NT" means that the compound was not tested at the indicated concentration.

The above example demonstrates that Compounds EH–IR, illustrative 5-Aryltetrazole Compounds, inhibit xanthine oxidase and, accordingly are useful for treating or preventing an inflammation disease, a reperfusion disease, hyperuricemia, gout, tumor-lysis syndrome, or an inflammatory bowel disorder.

5.14. Example 14

Toxic Liver Injury Model

Illustrative 5-Aryltetrazole Compounds exert hepatoprotective effects in a thioacetamide model of hepatic failure. The table below shows the efficacy of various illustrative 5-Aryltetrazole Compounds tested for their hepatoprotective activity in mice. Illustrated are percent inhibition of the increased serum AST levels resulting from an intraperitoneal injection of thioacetamide (400 mg/kg) following a single oral dose (3 mL/kg or 10 mL/kg) of various doses of 5-Aryltetrazole Compounds. Results are expressed as percent inhibtion, mean ±SEM (n=7–10). Studies were conducted as described in *Biochim. Biophys. Acta.* 1536(1): 21–30 (2001).

TOXIC LIVER INJURY MODEL

| | Percent Inhibition of Serum AST Levels | |
|---|---|---|
| Compound | 3 mg/kg | 10 mg/kg |
| HE | 3 ± 8 | 20 ± 5 |
| HI | 25 ± 4 | 46 ± 8 |
| HR | 23 ± 8 | 41 ± 8 |
| HU | NT | 33 ± 5 |
| IO | 12 ± 7 | 31 ± 7 |
| IP | 11 ± 7 | 31 ± 7 |
| IQ | 24 ± 9 | 36 ± 12 |
| HZ | NT | 31 ± 1 |

Accordingly, the above example demonstrates that Compounds HI, HR, HU, IO–IQ and HZ, illustrative 5-Aryltetrazole Compounds, inhibit serum AST levels and, accordingly, are useful for treating or preventing organ failure of various etiologies.

5.15. Example 15

Collagen-Induced Arthritis

An illustrative 5-Aryltetrazole Compound exerts protective effects in a model of collagen-induced arthritis in mice. Results are expressed as incidence and severity over time. Studies were conducted as described in *Inflamm. Res.* 50(11):561–569 (2001). The results illustrate that the administration of Compound IQ, an illustrative 5-Aryltetrazole Compound, reduced incidence of collagen-induced arthritis in mice. Specifically, after 33 days 100% of the untreated mice exhibited arthritis; however, mice that were administered Compound IQ showed a significant decrease in the incidence of collagen-induced arthritis.

| | Time (days) | | | | |
|---|---|---|---|---|---|
| | 25 | 27 | 29 | 31 | 33 |
| % Incidence Vehicle | 35 | 45 | 55 | 90 | 100 |
| Compound IQ | 20 | 35 | 45 | 75 | 85 |
| Mean Severity Vehicle | 0 | 0 | 8 | 10 | 12 |
| Compound IQ | 0 | 0 | 3 | 8 | 8 |

The above example demonstrates that Compound IQ, an illustrative 5-Aryltetrazole Compound, inhibits collagen-induced arthritis.

5.16. Example 16

Reperfusion Injury

Illustrative 5-Aryltetrazole Compounds exert protective effects in various models of organ ischemia and reperfusion. For example, intraperitoneal administration of illustrative 5-Aryltetrazole Compounds retard the progression of gut ischemia reperfusion-induced hyperpermeability and mortality in mice. Results are expressed as % decrease in gut hyperpermeability and as mortality as observed after 6 hours and 2 days of reperfusion. Studies were conducted as described in *Shock,* 14(2):134–141 (2000). There was a notable dose-dependent effect on gut hyperpermeability and there was an improvement in survival rate, as tested at the highest dose of both levels.

| | Dose | | | |
|---|---|---|---|---|
| | 3 mg/kg | 10 mg/kg | 30 mg/kg | 30 mg/kg |
| Aryltetrazole | None | HI | HI | HI | IQ |
| Gut Permeability | 100% | 73% | 69% | 47% | 39% |

| | Dose Compound | | |
|---|---|---|---|
| | No Aryltetrazole Administered | 30 mg/kg Compound HI | 30 mg/kg Compound IQ |
| Survival % (6 h) | 60 | 87 | 87 |
| Survival % (2days) | 0 | 20 | 13 |

The above example demonstrates that Compound HI and IQ, illustrative 5-Aryltetrazole Compounds, are useful for treating or preventing ischemia in an animal.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which have been incorporated herein in their entirety.

What is claimed is:

1. A method for treating an inflammation disease in an animal comprising administering to an animal in need thereof an effective amount of a compound of formula (Ib);

$$\text{(Ib)}$$

or a pharmaceutically acceptable salt or hydrate thereof, wherein:

$R_1$ is —$CO_2R_4$, —$C(O)R_5$, or $C(O)N(R_5)(R_5)$;

each $R_2$ is independently -halo, —$NO_2$, —CN, —OH, —$N(R_5)(R_5)$, —$OR_5$, —$C(O)R_5$, —$C(O)NHC(O)(R_5)$, —$OC(O)R_5$, —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_5-C_{10})$cycloalkenyl, —$(C_3-C_7)$heterocycle, —$(C_5)$heteroaryl, —$(C_6)$heteroaryl, -phenyl, -naphthyl, -benzyl, —$CO_2R_5$, —$C(O)OCH(R_5)(R_5)$, —$NHC(O)R_5$, —$NHC(O)NHR_5$, —$C(O)NHR_5$, —$OC(O)R_5$, —$OC(O)OR_5$, —$SR_5$, —$S(O)R_5$, or —$S(O)_2R_5$;

$R_3$ is —H, -halo, —$NO_2$, —CN, —OH, —$N(R_5)(R_5)$, —$O(CH_2)_mR_5$, —$C(O)R_5$, —$C(O)NR_5R_5$, —$C(O)NH(CH_2)_m(R_5)$, —$OCF_3$, -benzyl, —$CO_2CH(R_5)(R_5)$, —$(C_1-C_{10})$alkyl, —$(C_2-C_{10})$alkenyl, —$(C_2-C_{10})$alkynyl, —$(C_3-C_{10})$cycloalkyl, or —$(C_8-C_{14})$bicycloalkyl;

$R_4$ is —$CF_3$, —$(C_1-C_{10})$alkyl, -benzyl, -adamantyl, -morpholinyl, -pyrrolidyl, -pyrridyloxide, -pyrrolidinyldione, -piperidinyl, —$(C_5)$heteroaryl, —$(C_6)$heteroaryl, —$(C_2-C_{10})$alkenyl, —$(C_2-C_{10})$alkynyl, —$(C_3-C_{10})$cycloalkyl, —$(C_8-C_{14})$bicycloalkyl, —$(C_3-C_{10})$heterocycle, or $$\text{(R}_6\text{)}_p;$$

each $R_5$ is independently H or $R_4$;

each $R_6$ is independently -halo, —$NO_2$, —CN, —OH, —$CO_2H$, —$N(C_1-C_{10})$alkyl$(C_1-C_{10})$alkyl, —$O(C_1-C_{10})$alkyl, —$C(O)(C_1-C_{10})$alkyl, —$C(O)NH(CH_2)_m(C_1-C_{10})$alkyl, —$OCF_3$, -benzyl, —$CO_2(CH_2)_m$ $CH((C_1-C_{10})$alkyl$(C_1-C_{10})$alkyl), —C(O)H, —$CO_2(C_1-C_{10})$alkyl, —$(C_1-C_{10})$alkyl, —$(C_2-C_{10})$alkenyl, —$(C_2-C_{10})$alkynyl, —$(C_3-C_{10})$cycloalkenyl, —$(C_8-C_{14})$bicycloalkyl, —$(C_5-C_{10})$cycloalkenyl, —$(C_5)$heteroaryl, —$(C_6)$heteroaryl, -phenyl, -naphthyl, —$(C_3-C_{10})$heterocycle, —$CO_2(CH_2)_m(C_1-C_{10})$alkyl, —$CO_2(CH_2)_mH$, —$NHC(O)(C_1-C_{10})$alkyl, —$NHC(O)NH(C_1-C_{10})$alkyl, —$OC(O)(C_1-C_{10})$alkyl, —$OC(O)O(C_1-C_{10})$alkyl, or —$SO_2NH_2$;

n is an integer ranging from 0 to 4;

each m is independently an integer ranging from 0 to 8; and each p is independently an integer ranging from 0 to 5.

2. The method of claim 1, wherein:
$R_1$ is —$CO_2R_5$.

3. The method of claim 1, wherein:
$R_1$ is —$C(O)R_5$.

4. The method of claim 1, wherein:
$R_1$ is —$C(O)N(R_5)(R_5)$.

5. The method of claim 1, wherein:
n is 0; and
$R_3$ is —$C(O)NHR_5$.

6. The method of claim 5, wherein:
$R_5$ is $$\text{(R}_6\text{)}_p.$$

7. The method of claim 6, wherein:
p is an integer from 1 to 3.

8. The method of claim 7, wherein:
each $R_6$ is independently halo.

9. The method of claim 1, wherein the animal is human.

10. A method for treating a reperfusion disease in an animal comprising administering to an animal in need thereof an effective amount of a compound of formula (Ib):

$$\text{(Ib)}$$

or a pharmaceutically acceptable salt or hydrate thereof, wherein:

$R_1$ is H, —$CO_2R_4$, $C(O)R_5$, or $C(O)N(R_5)(R_5)$;

each $R_2$ is independently -halo, —$NO_2$, —CN, —OH, —$N(R_5)(R_5)$, —$OR_5$, —$C(O)R_5$, —$C(O)NHC(O)R_5$, —$OC(O)R_5$, —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_5-C_{10})$cycloalkenyl, —$(C_3-C_7)$heterocycle, —$(C_5)$heteroaryl, —$(C_6)$heteroaryl, -phenyl, -naphthyl, -benzyl, —$CO_2R_5$, —$C(O)OCH(R_5)(R_5)$, —$NHC(O)R_5$, —$NHC(O)NHR_5$, —$C(O)NHR_5$, —$OC(O)R_5$, —$OC(O)OR_5$, —$SR_5$, —$S(O)R_5$, or —$S(O)_2R_5$;

$R_3$ is —H, -halo, —$NO_2$, —CN, —OH, —$N(R_5)(R_5)$, —$O(CH_2)_mR_5$, —$C(O)R_5$, —$C(O)NR_5R_5$, —$C(O)NH(CH_2)_m(R_5)$, —$OCF_3$, -benzyl, —$CO_2CH(R_5)(R_5)$, —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_5-C_{10})$cycloalkenyl, —$(C_5)$heteroaryl, —$(C_6)$heteroaryl, -naphthyl, —$(C_3-C_{10})$heterocycle, —$CO_2(CH_2)_mR_5$, —$NHC(O)R_5$, —$NHC(O)R_5$, —$NHC(O)NHR_5$, —$OC(O)(CH_2)_mCHR_5R_5$, —$CO_2(CH_2)_mCHR_5R_5$, —$OC(O)OR_5$, —$SR_5$, —$S(O)R_5$, —$S(O)_2R_5$, —$S(O)_2NHR_5$;

R₄ is -pyrridyloxide, -pyrrolidinyldione, -piperidinyl, —(C₅)heteroaryl, —(C₆)heteroaryl, —(C₂–C₁₀)alkenyl, —(C₂–C₁₀)alkynyl, —(C₃–C₁₀)cycloalkyl, —(C₈–C₁₄)bicycloalkyl, —(C₃–C₁₀)heterocycle, or

each R₅ is independently H or R₄;
each R₆ is independently -halo, —NO₂, —CN, —OH, —CO₂H, —N(C₁–C₁₀)alkyl(C₁–C₁₀)alkyl, —O(C₁–C₁₀)alkyl, —C(O)(C₁–C₁₀)alkyl, —C(O)NH(CH₂)ₘ(C₁–C₁₀)alkyl, —OCF₃, -benzyl, —CO₂(CH₂)ₘ CH((C₁–C₁₀)alkyl(C₁–C₁₀)alkyl), —C(O)H, —CO₂(C₁–C₁₀)alkyl, —(C₁–C₁₀)alkyl, —(C₂–C₁₀)alkenyl, —(C₂–C₁₀)alkynyl, —(C₃–C₁₀)cycloalkyl, —(C₈–C₁₄)bicycloalkyl, —(C₅–C₁₀)cycloalkenyl, —(C₅)heteroaryl, —(C₆)heteroaryl, -phenyl, naphthyl, —(C₃–C₁₀)heterocycle, —CO₂(CH₂)ₘ(C₁–C₁₀)alkyl, —CO₂(CH₂)ₘH, —NHC(O)(C₁–C₁₀)alkyl, —NHC(O)NH(C₁–C₁₀)alkyl, —OC(O)(C₁–C₁₀)alkyl, —OC(O)O(C₁–C₁₀)alkyl, and —SO₂NH₂;
n is an integer ranging from 0 to 4;
each m is independently an integer ranging from 0 to 8; and
each p is independently an integer ranging from 0 to 5, with the proviso that the compound of Formula (Ib) is not:

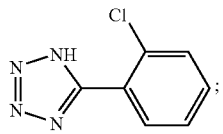

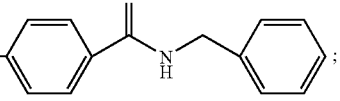

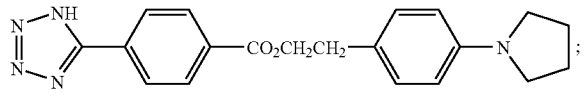

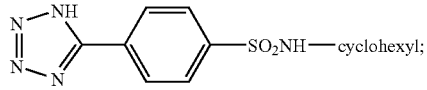

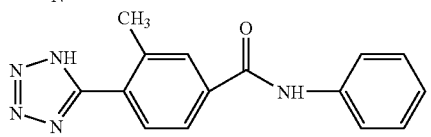

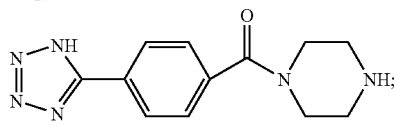

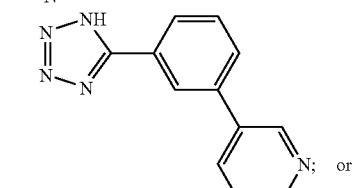

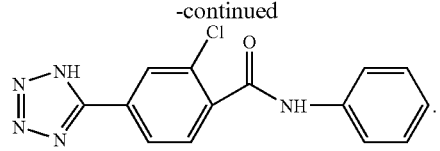

11. The method of claim 10, wherein:
R₁ is H.
12. The method of claim 10, wherein:
R₁ is —CO₂R₅.
13. The method of claim 10, wherein:
R₁ is —C(O)R₅.
14. The method of claim 10, wherein:
R₁ is —C(O)N(R₅)(R₅).
15. The method of claim 10, wherein:
n is 0; and
R₃ is —C(O)NHR₅.
16. The method of claim 15, wherein:
R₅ is

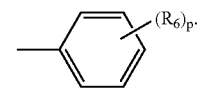

17. The method of claim 16, wherein:
p is an integer from 1 to 3.
18. The method of claim 17, wherein:
each R₆ is independently halo.
19. The method of claim 10, wherein the animal is human.
20. A method for treating hyperuricemia or gout in an animal comprising administering to an animal in need thereof an effective amount of a compound of formula (Ib):

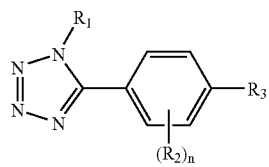

(Ib)

or a pharmaceutically acceptable salt or hydrate thereof, wherein:
R₁ is —H, CO₂R₄; C(O)R₅, or C(O)N(R₅)(R₅);
each R₂ is independently -halo, —NO₂, —CN, —OH, —N(R₅)(R₅), —OR₅, —C(O)R₅, —C(O)NHC(O)R₅, —OC(O)R₅, —(C₁–C₁₀)alkyl, —(C₂–C₁₀)alkenyl, —(C₂–C₁₀)alkynyl, —(C₃–C₁₀)cycloalkyl, —(C₈–C₁₄)bicycloalkyl, —(C₅–C₁₀)cycloalkenyl, —(C₃–C₇)heterocycle, —(C₅)heteroaryl, —(C₆)heteroaryl, -phenyl, -naphthyl, -benzyl, —CO₂R₅, —C(O)OCH(R₅)(R₅), —NHC(O)R₅, —NHC(O)NHR₅, —C(O)NHR₅, —OC(O)R₅, —OC(O)OR₅, —SR₅, —S(O)R₅, or —S(O)₂R₅;
R₃ is —H, -halo, —NO₂, —CN, —OH, —N(R₅)(R₅), —O(CH₂)ₘR₅, —C(O)R₅, —C(O)NR₅R₅, —C(O)NH(CH₂)ₘ(R₅), —OCF₃, -benzyl, —CO₂CH(R₅)(R₅), —(C₁–C₁₀)alkyl, R₄ is —CF₃, —(C₁–C₁₀)alkyl, -benzyl, -adamantyl, -morpholinyl, -pyrrolidyl, -pyrridyloxide, -pyrrolidinyldione, -piperidinyl, —(C₅)heteroaryl, —(C₆)heteroaryl, or ![structure with (R₆)ₚ on phenyl]

each R₅ is independently H or R₄;
each R₆ is independently -halo, —NO₂, —CN, —OH, —CO₂H, —N(C₁–C₁₀)alkyl(C₁–C₁₀)alkyl, —O(C₁–C₁₀)alkyl, —C(O)(C₁–C₁₀)alkyl, —C(O)NH(CH₂)ₘ(C₁–C₁₀)alkyl, —OCF₃, -benzyl, —CO₂(CH₂)ₘ CH((C₁–C₁₀)alkyl(C₁–C₁₀)alkyl), —C(O)H, —CO₂(C₁–C₁₀)alkyl, —(C₁–C₁₀)alkyl, —(C₂–C₁₀)alkenyl, —(C₂–C₁₀)alkynyl, —(C₃–C₁₀)cycloalkyl, —(C₈–C₁₄)bicycloalkyl, —(C₅–C₁₀)cycloalkenyl, —(C₅)heteroaryl, —(C₆)heteroaryl, -phenyl, naphthyl, —(C₃–C₁₀)heterocycle, —CO₂(CH₂)ₘ(C₁–C₁₀)alkyl, —CO₂(CH₂)ₘH, —NHC(O)(C₁–C₁₀)alkyl, —NHC(O)NH(C₁–C₁₀)alkyl, —OC(O)(C₁–C₁₀)alkyl, —OC(O)O(C₁–C₁₀)alkyl, or —SO₂NH₂;

n is an integer ranging from 0 to 4;
each m is independently an integer ranging from 0 to 8; and
each p is independently an integer ranging from 0 to 5,
with the proviso that the compound of Formula (Ib) is not:

![structure: tetrazole-phenyl-Cl]

![structure: tetrazole-phenyl-C(O)NH-CH₂-phenyl]

![structure: tetrazole-phenyl-CO₂CH₂CH₂-phenyl-N-pyrrolidine]

![structure: tetrazole-phenyl-pyridine]

![structure: tetrazole-phenyl(Cl)-C(O)NH-phenyl]

![structure: tetrazole-phenyl(CH₃)-C(O)NH-phenyl]; or

![structure: tetrazole-phenyl-C(O)N(CH₃)-phenyl]

21. The method of claim 20 wherein:
R₁ is H.
22. The method of claim 20, wherein:
R₁ is —CO₂R₅.
23. The method of claim 20, wherein:
R₁ is —C(O)R₅.
24. The method of claim 20, wherein:
R₁ is —C(O)N(R₅)(R₅).
25. The method of claim 20, wherein:
n is 0; and
R₃ is —C(O)NHR₅.
26. The method of claim 25, wherein:
R₅ is ![structure with (R₆)ₚ on phenyl]

27. The method of claim 26, wherein:
p is an integer from 1 to 3.
28. The method of claim 27, wherein:
each R₆ is independently halo.
29. The method of claim 20, wherein the animal is human.
30. A method for treating colitis in an animal comprising administering to an animal in need thereof an effective amount of a compound of formula (Ib):

(Ib)

![structure of formula Ib: tetrazole with R₁, phenyl with (R₂)ₙ, and R₃]

or a pharmaceutically acceptable salt or hydrate thereof, wherein:
R₁ is —CO₂R₄; C(O)R₅, or C(O)N(R₅)(R₅);
each R₂ is independently -halo, —NO₂, —CN, —OH, N(R₅)(R₅), —OR₅, —C(O)R₅, —C(O)NHC(O)R₅, —OC(O)R₅, —(C₁–C₁₀)alkyl, —(C₂–C₁₀)alkenyl, —(C₂–C₁₀)alkynyl, —(C₃–C₁₀)cycloalkyl, —(C₈–C₄₁)bicycloalkyl, —(C₅–C₁₀)cycloalkenyl, —(C₃–C₇)heterocycle, —(C₅)heteroaryl, —(C₆)heteroaryl, -phenyl, -naphthyl, -benzyl, —CO₂R₅, —C(O)OCH(R₅)(R₅), —NHC(O)R₅, —NHC(O)NHR₅, —C(O)NHR₅, —OC(O)R₅, —OC(O)OR₅, —SR₅, —S(O)R₅, or —S(O)₂R₅;
R₃ is —C(O)NR₅R₅;
R₄ is —CF₃, —(C₁–C₁₀)alkyl, -benzyl, -adamantyl, -morpholinyl, -pyrrolidyl, -pyrridyloxide, -pyrrolidinyldione, -piperidinyl, —(C₅)heteroaryl, —(C₆)heteroaryl, —(C₂–C₁₀)alkenyl, —(C₂–C₁₀)alkynyl, —(C₃–C₁₀)cycloalkyl, —(C₈–C₁₄)bicycloalkyl, or

each $R_5$ is independently H or $R_4$;

each $R_6$ is independently -halo, —$NO_2$, —CN, —OH, —$CO_2H$, —N($C_1$–$C_{10}$)alkyl, ($C_1$–$C_{10}$)alkyl, —O($C_1$–$C_{10}$)alkyl, —C(O)($C_1$–$C_{10}$)alkyl, —C(O)NH ($CH_2$)$_m$($C_1$–$C_{10}$)alkyl, —$OCF_3$, -benzyl, $CO_2(CH_2)_m$ CH(($C_1$–$C_{10}$)alkyl($C_1$–$C_{10}$)alkyl), —C(O)H, —$CO_2$ ($C_1$–$C_{10}$)alkyl, —($C_1$–$C_{10}$)alkyl, —($C_2$–$C_{10}$)alkenyl, —($C_2$–$C_{10}$)alkynyl, —($C_3$–$C_{10}$)cycloalkyl, —($C_8$–$C_{14}$)bicycloalkyl, —($C_5$–$C_{10}$)cycloalkenyl, —($C_5$)heteroaryl, —($C_6$)heteroaryl, -phenyl, -naphthyl, —($C_3$–$C_{10}$)heterocycle, —$CO_2(CH_2)_m$($C_1$–$C_{10}$) alkyl, —$CO_2(CH_2)_m$H, —NHC(O)($C_1$–$C_{10}$)alkyl, —NHC(O)NH($C_1$–$C_{10}$)alkyl, —OC(O)($C_1$–$C_{10}$)alkyl, —OC(O)O($C_1$–$C_{10}$)alkyl, or —$SO_2NH_2$;

n is an integer ranging from 0 to 4;

each m is independently an integer ranging from 0 to 8; and each p is independently an integer ranging from 0 to 5.

31. The method of claim 30, wherein:
$R_1$ is —$CO_2R_5$.

32. The method of claim 30, wherein:
$R_1$ is —C(O)$R_5$.

33. The method of claim 30, wherein:
$R_1$ is —C(O)N($R_5$)($R_5$).

34. The method of claim 30, wherein:
n is 0; and
$R_3$ is —C(O)NH$R_5$.

35. The method of claim 34, wherein:
$R_5$ is

36. The method of claim 35, wherein:
p is an integer from 1 to 3.

37. The method of claim 31, wherein:
each $R_6$ is independently halo.

38. The method of claim 30, wherein the animal is human.

39. A method for treating an inflammation disease, comprising administering to an animal in need thereof an effective amount of a compound of formula:

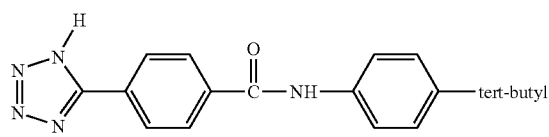

or a pharmaceutically acceptable salt or hydrate thereof.

40. The method of claim 10, wherein the compound has the formula:

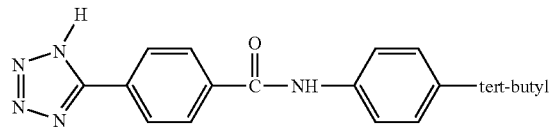

or a pharmaceutically acceptable salt or hydrate thereof.

41. The method of claim 20, wherein the compound has the formula:

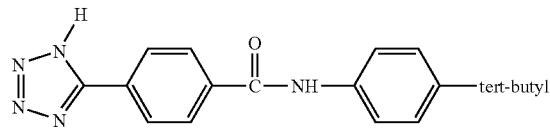

or a pharmaceutically acceptable salt or hydrate thereof.

42. A method for treating colitis, comprising administering to an animal in need thereof an effective amount of a compound of formula:

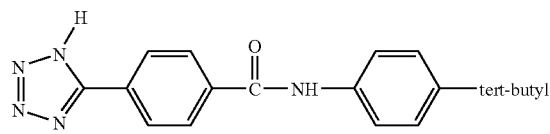

or a pharmaceutically acceptable salt or hydrate thereof.

43. A method for treating an inflammation disease, comprising administering to an animal in need thereof an effective amount of a compound of formula (Ib):

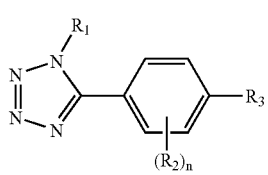

(Ib)

or a pharmaceutically acceptable salt or hydrate thereof, wherein:
$R_1$ is —H;
$R_3$ is —C(O)NH($R_5$);
$R_5$ is

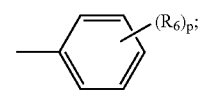

each $R_6$ is independently -halo;
n is 0; and
each p is independently an integer ranging from 1 to 3.

44. The method of claim 10, wherein:
$R_1$ is —H; and
each $R_6$ is independently -halo.

45. The method of claim 20, wherein:
R₁ is —H; and
each R₆ is independently -halo.

46. A method for treating colitis, comprising administering to an animal in need thereof an effective amount of a compound of formula (Ib):

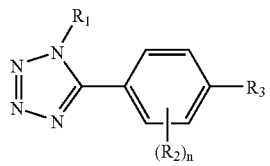
(Ib)

or a pharmaceutically acceptable salt or hydrate thereof, wherein:
R₁ is —H;
R₃ is —C(O)NH(R₅);
R₅ is

each R₆ is independently -halo;
n is 0; and
each p is independently an integer ranging from 1 to 3.

47. The method of claim 10, wherein the compound of formula (Ib) is:

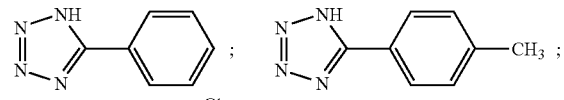

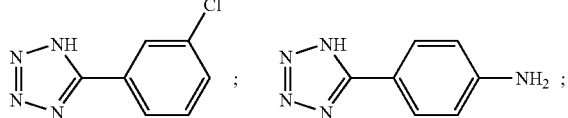

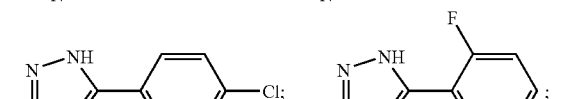

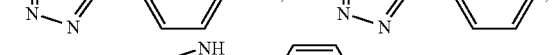

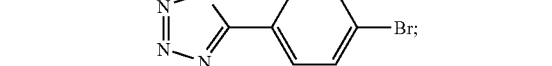

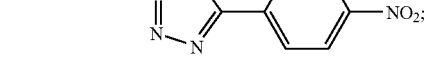

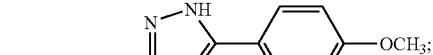

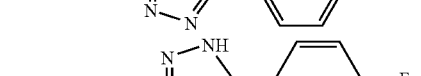

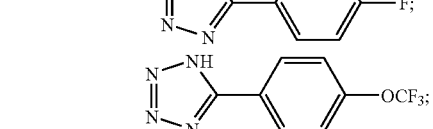

-continued

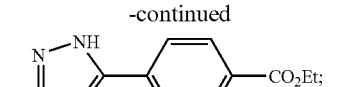

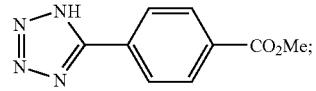

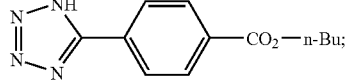

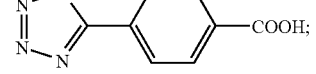

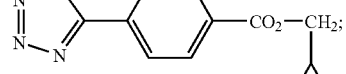

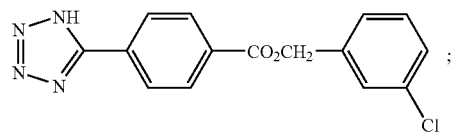

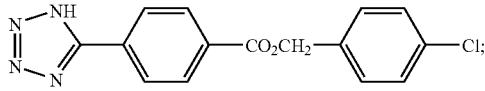

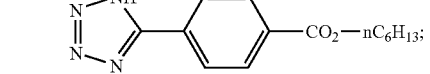

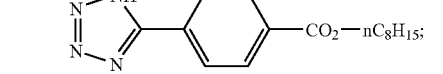

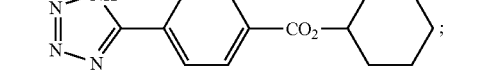

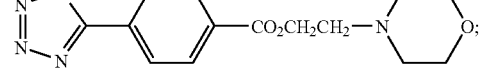

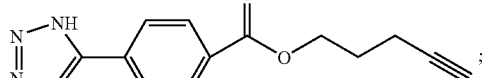

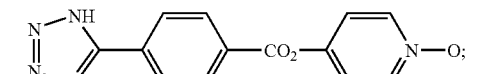

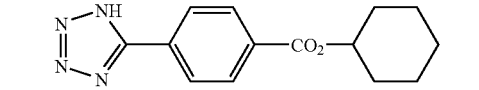

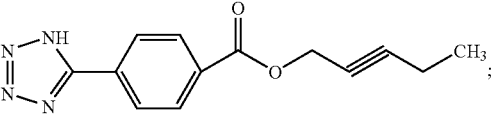

-continued
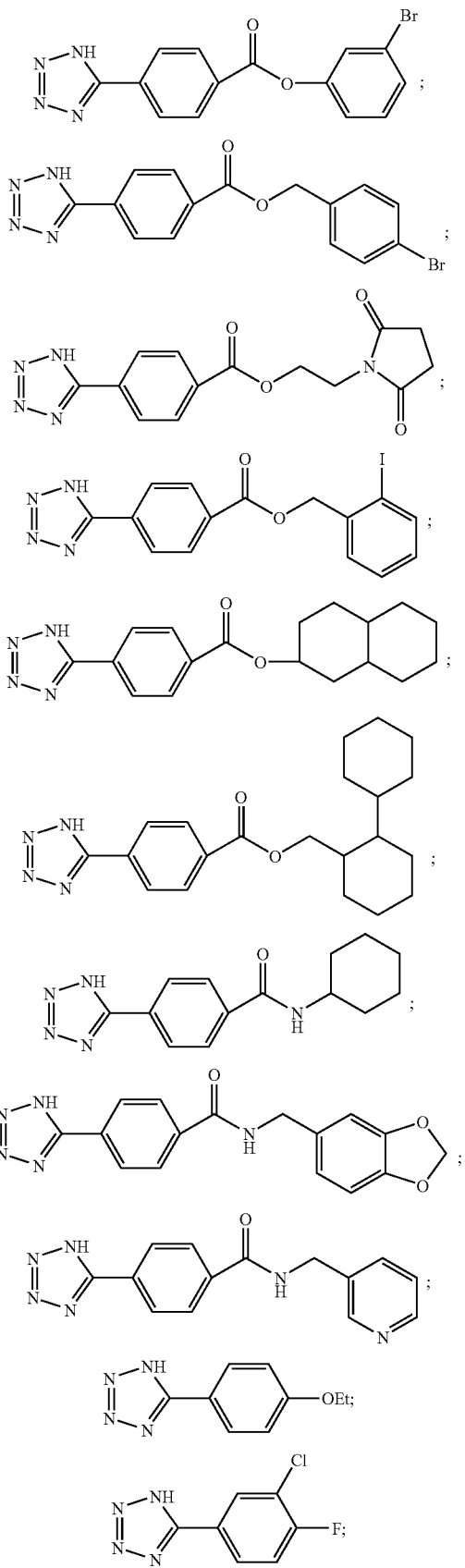
-continued
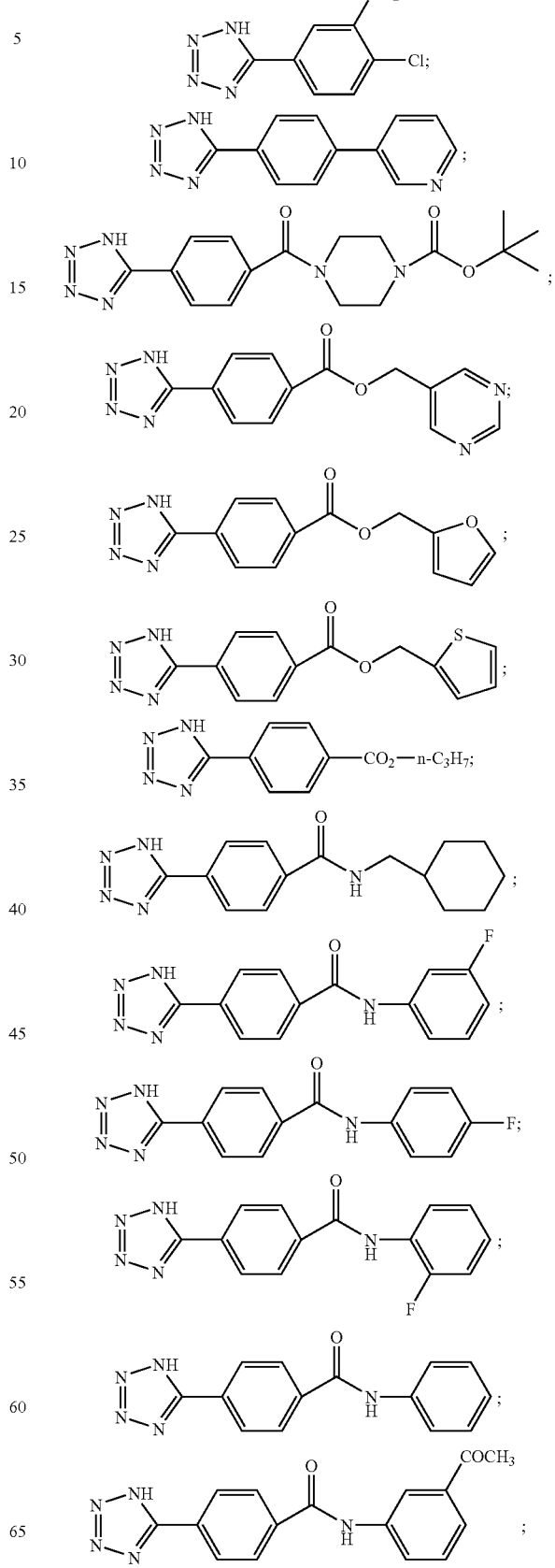

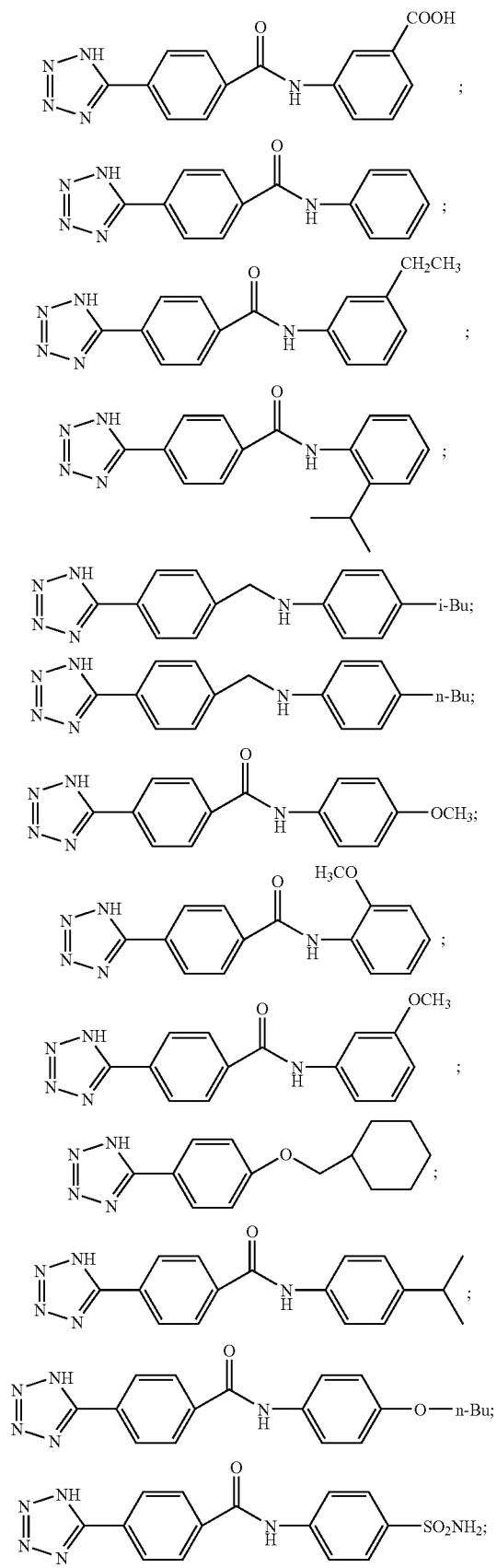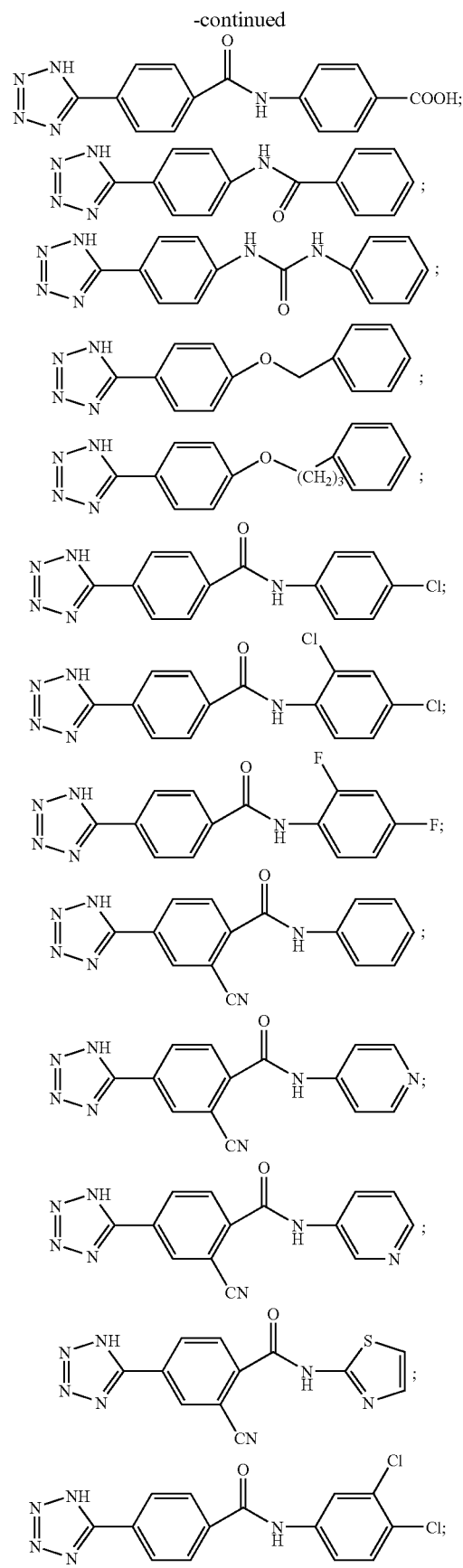

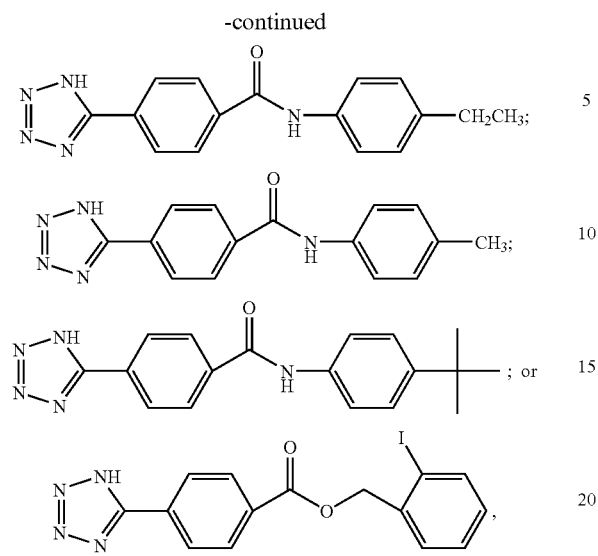
or a pharmaceutically acceptable salt or hydrate thereof.
48. The method of claim 20, wherein the compound of formula (Ib) is:
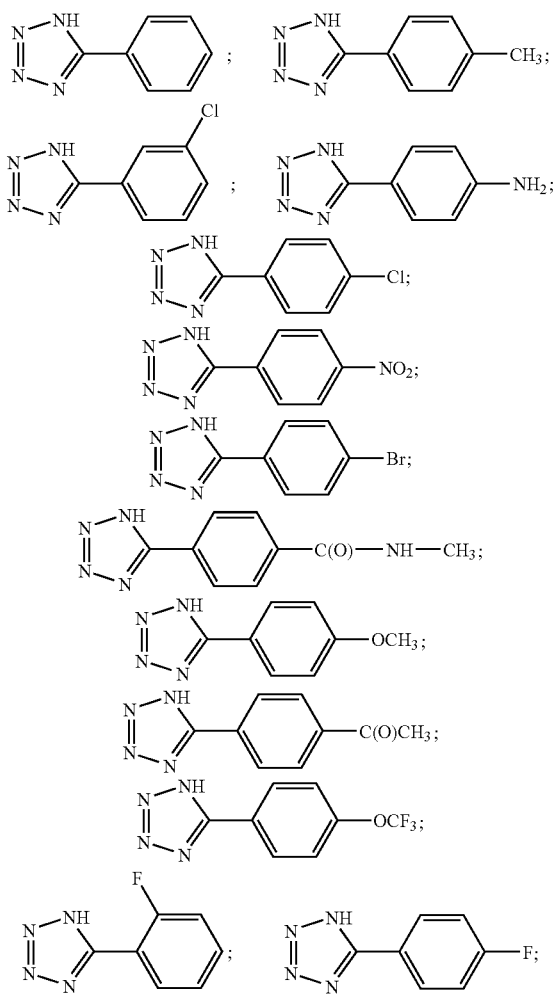
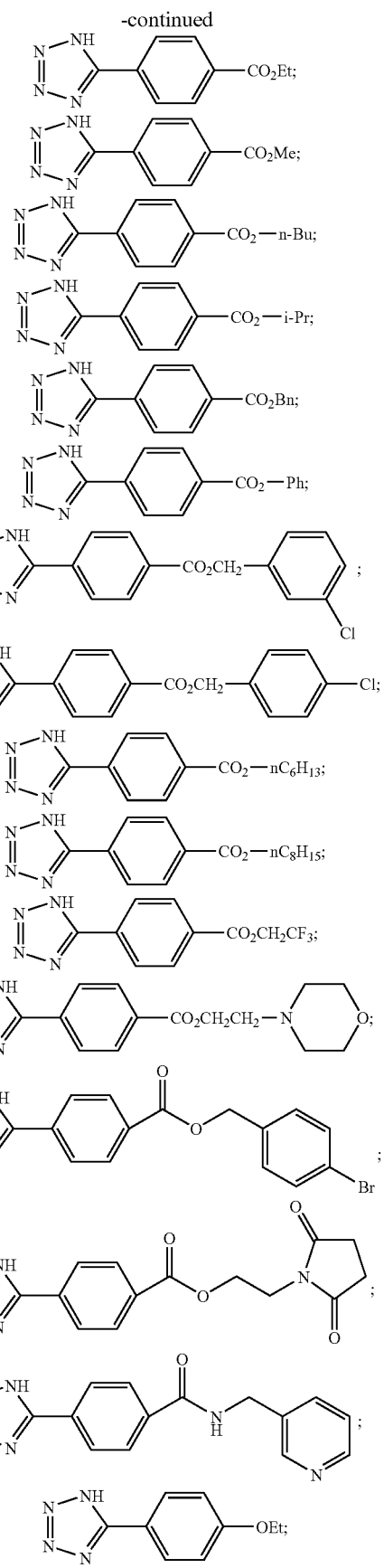

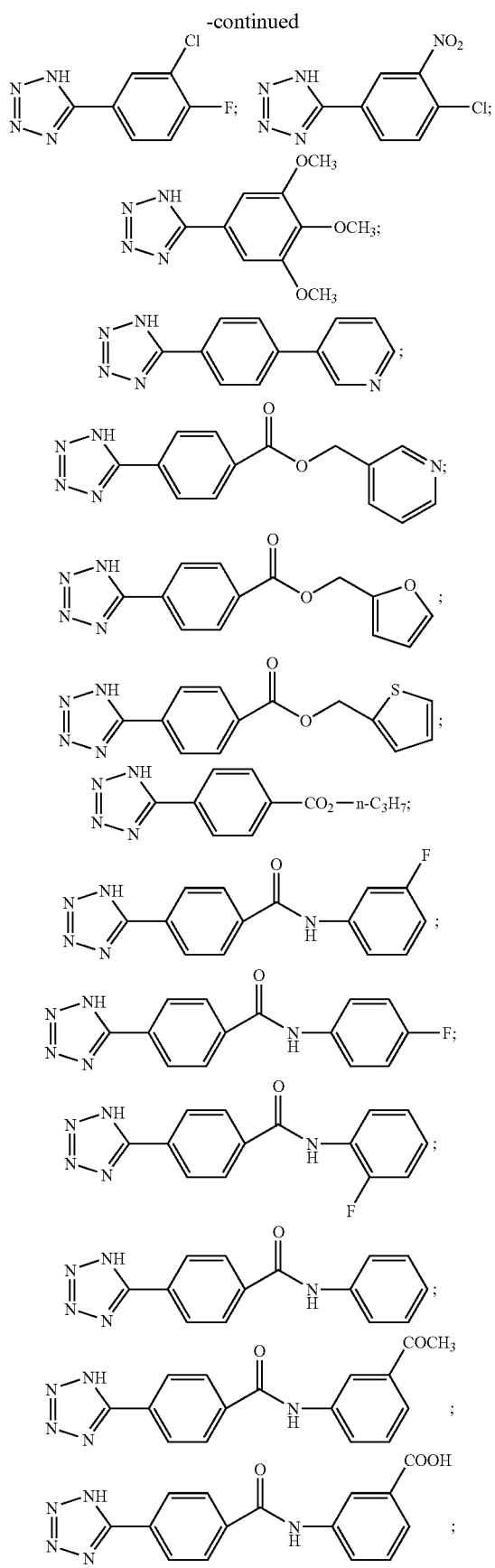
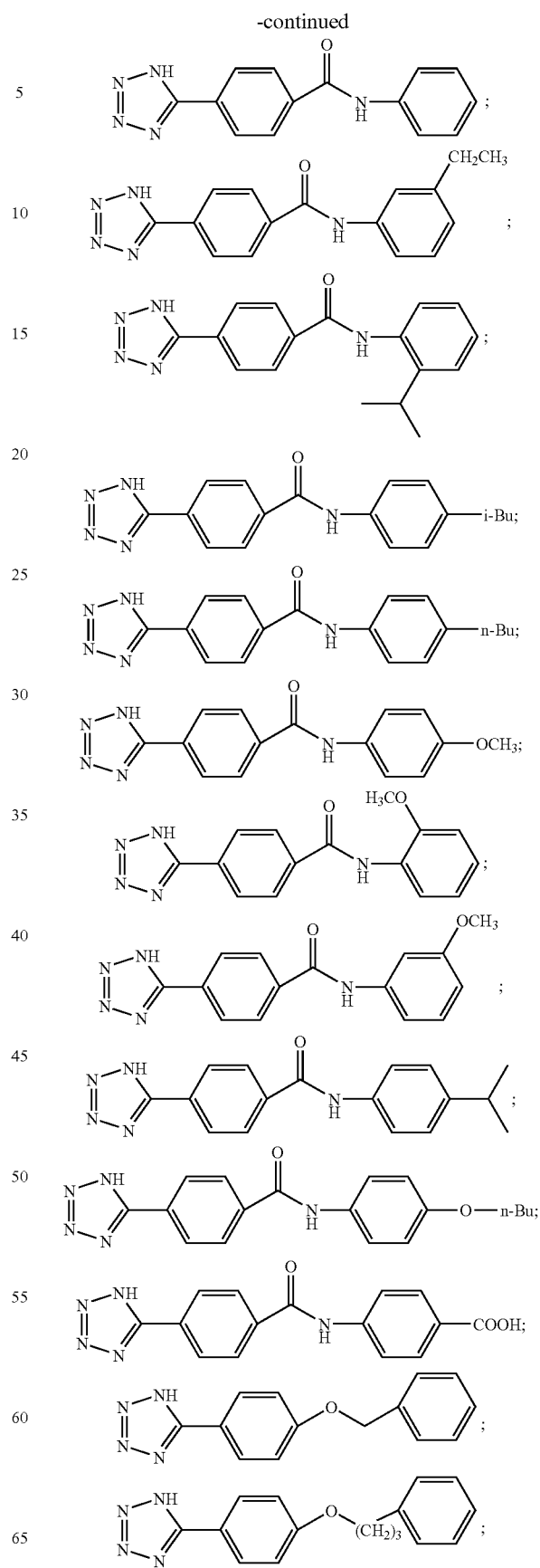

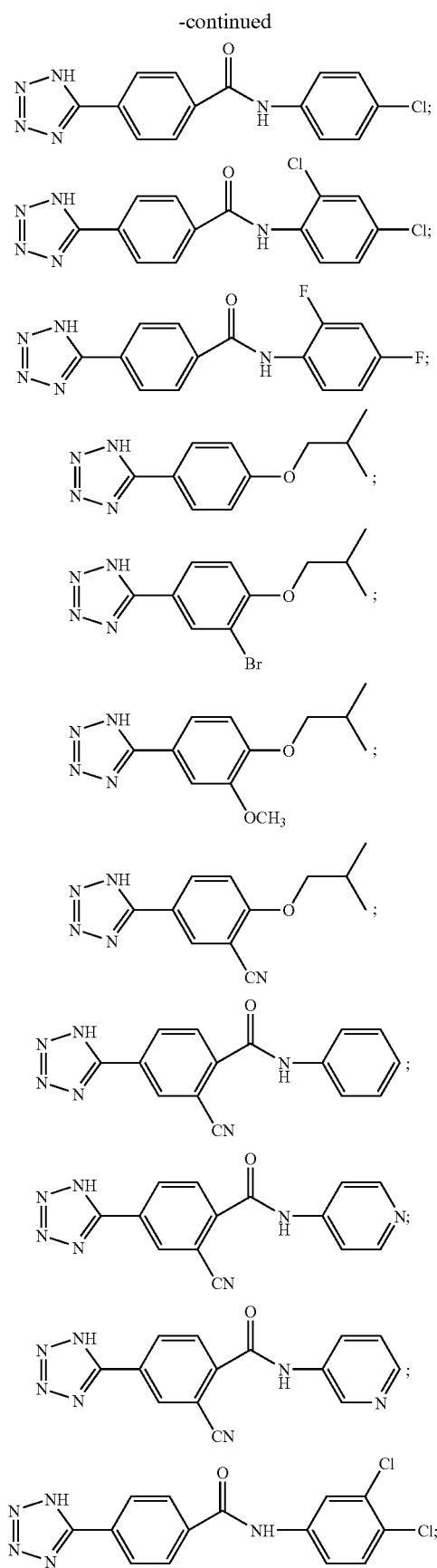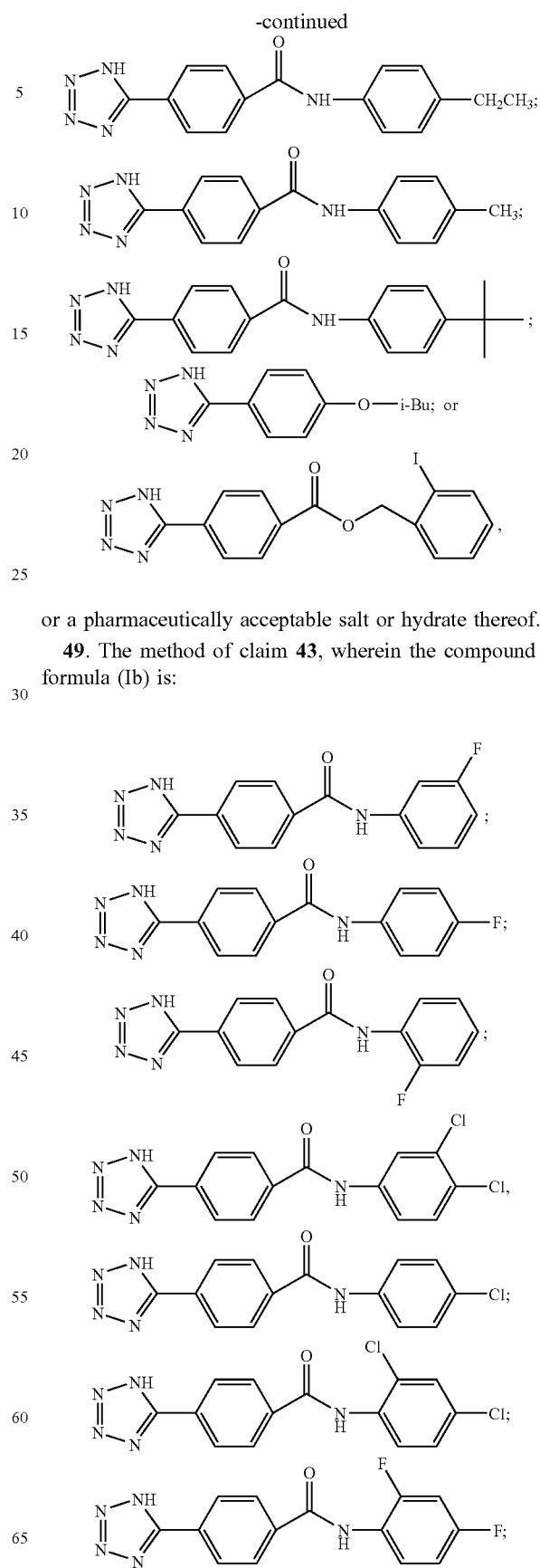
or a pharmaceutically acceptable salt or hydrate thereof.
49. The method of claim 43, wherein the compound of formula (Ib) is:

-continued
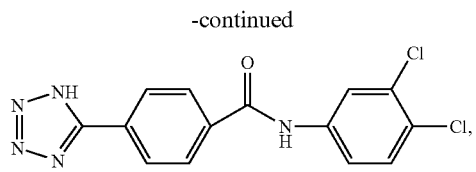
or a pharmaceutically acceptable salt or hydrate thereof.
50. The method of claim 46, wherein the compound of formula (Ib) is:
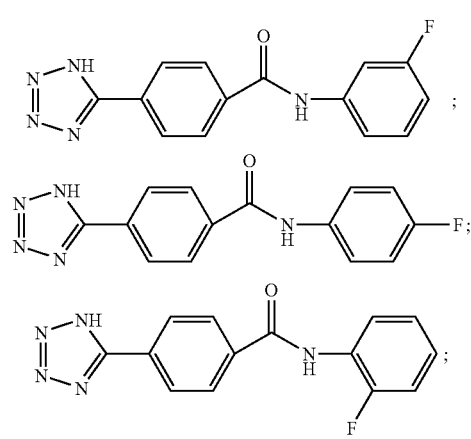
-continued
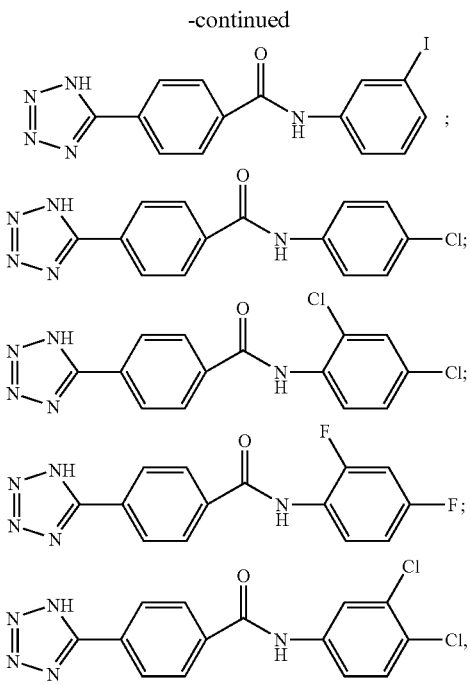
or a pharmaceutically acceptable salt or hydrate thereof.
* * * * *